US006627657B1

(12) United States Patent
Hilgren et al.

(10) Patent No.: US 6,627,657 B1
(45) Date of Patent: Sep. 30, 2003

(54) PEROXYCARBOXYLIC ACID COMPOSITIONS AND METHODS OF USE AGAINST MICROBIAL SPORES

(75) Inventors: John D. Hilgren, Shoreview, MN (US); Francis L. Richter, Lino Lakes, MN (US); Duane J. Reinhardt, Maplewood, MN (US); Joy A. Salverda, Woodbury, MN (US); Christina L. Rahm, Newport, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/532,691

(22) Filed: Mar. 22, 2000

(51) Int. Cl.$^7$ .................. A01N 37/00; A01N 37/10; A01N 37/08; A61K 31/185; A61K 31/19

(52) U.S. Cl. .................. 514/553; 514/557; 514/568; 514/572

(58) Field of Search .................. 424/600; 514/553, 514/557, 568, 572

(56) References Cited

U.S. PATENT DOCUMENTS

| | | | | |
|---|---|---|---|---|
| 4,051,058 A | | 9/1977 | Bowing et al. ............. | 252/186 |
| 4,051,059 A | * | 9/1977 | Bowing et al. ............. | 252/186 |
| 4,404,040 A | | 9/1983 | Wang ...................... | 134/22.14 |
| 4,654,208 A | | 3/1987 | Stockel et al. ............. | 424/78 |
| 5,078,896 A | | 1/1992 | Rorig et al. ............... | 252/102 |
| 5,200,189 A | | 4/1993 | Oakes et al. .............. | 424/405 |
| 5,279,735 A | | 1/1994 | Cosentino et al. ........ | 210/321.69 |
| 5,314,687 A | | 5/1994 | Oakes et al. .............. | 424/405 |
| 5,320,805 A | | 6/1994 | Kramer et al. ............ | 422/28 |
| 5,435,808 A | * | 7/1995 | Holzhauer et al. ........ | 8/94.18 |
| 5,436,008 A | | 7/1995 | Richter et al. ............. | 424/405 |
| 5,489,434 A | | 2/1996 | Oakes et al. .............. | 424/405 |
| 5,545,374 A | | 8/1996 | French et al. ............. | 422/28 |
| 5,567,444 A | | 10/1996 | Hei et al. ................. | 424/616 |
| 5,683,724 A | | 11/1997 | Hei et al. ................. | 424/616 |
| 5,718,910 A | | 2/1998 | Oakes et al. .............. | 424/405 |
| 5,780,064 A | | 7/1998 | Meisters et al. ........... | 424/616 |
| 5,858,443 A | | 1/1999 | Hei et al. ................. | 426/506 |
| 6,183,708 B1 | * | 2/2001 | Hei et al. ................. | 423/210 |

FOREIGN PATENT DOCUMENTS

| | | |
|---|---|---|
| DE | 28 15 400 A1 | 10/1979 |
| DE | 39 29 335 A1 | 3/1991 |
| EP | 0 357 238 A2 | 3/1990 |
| EP | 0 488 090 A1 | 6/1992 |
| FR | 2 373 292 | 11/1977 |
| GB | 2255507 | * 11/1992 |
| RU | 2102447 | 1/1998 |
| WO | WO 93/01716 | 2/1993 |
| WO | WO 94/00548 | 1/1994 |
| WO | WO 94/06294 | 3/1994 |
| WO | WO 94/23575 | 10/1994 |
| WO | WO 00/30690 | 6/2000 |
| WO | WO 00/69778 | 11/2000 |

OTHER PUBLICATIONS

Alasri et al., "Bactericidal properties of peracetic acid and hydrogen, peroxide, along and in combination, and chlorine and formaldehyde against bacterial water strains", *Canadian Journal of Microbiology*, vol. 38, No. 7, pp. 635–642 (1992).
Blakistone et al., "Efficacy of Oxonia Active Against Selected Spore Formers", *Journal of Food Protection*, vol. 62, No. 3, pp. 262–267 (1999).
Fraser, "Novel applications of peracetic acid in industrial disinfection", *Speciality Chemicals*, vol. 7, No. 3, pp. 178–186 (1987).
Krzywicka, "Disinfectant activity of peracetic acid on the spores of bacteria", *Rocz. Panstw. Zakl. Hig.*, vol. 21, No. 6, pp. 595–599 (1970) with attached English summary.
International Search Report from the European Patent Office mailed on Oct. 12, 2001.
Blakistone, B. et al., "Efficacy of Oxonia Active Against Selected Spore Formers", *Journal of Food Protection*, vol. 62, No. 3, pp. 262–267 (1999).
Baldry, M., "The bactericidal, fungicidal and sporicidal properties of hydrogen peroxide and peracetic acid", *Journal of Applied Bacteriology*, vol. 54, pp. 417–423 (1993).
Notermans, S. et al., "A risk assessment study of *Bacillus cereus* present in pasteurized milk", *Food Microbiology*, vol. 14, pp. 143–151 (1997).
Hilgren, J. et al., "The Effect of Hydrogen Peroxide and Acetic Concentration on the Sporicidal Efficacy of 150 ppm Peracetic Acid at 60°C", *Microbiological Services Report—Ecolab Inc.*, (Completion date Oct. 1, 1996).

* cited by examiner

Primary Examiner—Alton N. Pryor
(74) Attorney, Agent, or Firm—Merchant & Gould P.C.

(57) ABSTRACT

Compositions having antimicrobial activity against a variety of microorganisms, including vegetative bacteria, bacterial spores, fungi, and fungal spores are particularly useful for microbiocidal treatments of a variety of substances. More specifically, compositions have antibmicrobial activity against microorganisms of the *Bacillus cereus* group such as *Bacillus cereus, Bacillus mycoides, Bacillus anthracis*, and *Bacillus thuringiensis* are particularly useful. Compositions including hydrogen peroxide, a carboxylic acid, and a peroxycarboxylic acid in which the weight ratio of the peroxycarboxylic acid to the hydrogen peroxide is at least 4:1 are effective against microorganisms, particularly bacterial spores. Such compositions include a reduced amount of hydrogen peroxide relative to the amount of peroxycarboxylic acid as compared to conventional compositions. Compositions can also include a quaternary ammonium compound, a stabilizing agent, a surfactant, a hydrotrope, or other additives. Methods of using a composition including hydrogen peroxide, a carboxylic acid, and a peroxycarboxylic acid in which the ratio of the peroxycarboxylic acid to the hydrogen peroxide is at least 4:1 are useful for reducing the microbial numbers on a variety of substances contaminated by microorganisms, particularly of the *Bacillus cereus* group. Such substances include foodstuffs, water, general-premise surfaces, specific-equipment surfaces, animal carcasses, soil, and textiles.

65 Claims, 1 Drawing Sheet

PEROXYCARBOXYLIC ACID COMPOSITIONS AND METHODS OF USE AGAINST MICROBIAL SPORES

FIELD OF THE INVENTION

The invention is generally directed to a composition having antimicrobial activity, including activity against microbial spores. More particularly, a composition of the invention includes hydrogen peroxide, a carboxylic acid, and a peroxycarboxylic acid and has a weight ratio of a peroxycarboxylic acid to hydrogen peroxide of at least 4:1. A composition of the invention is particularly useful for microbiocidal treatment of substances being contaminated with microorganisms of the Bacillus cereus group.

BACKGROUND OF THE INVENTION

A variety of industries such as, for example, the food industry, health-care industry, institutional industry, and hospitality industry, have a need to use antimicrobial treatments to reduce microbial populations in the environments in which these industries are carried out. In some instances, these antimicrobial treatments include the use of peracid materials.

Compositions for peracid materials and their use for reducing microbial populations are known. For example, Grosse-Bowing et al. (U.S. Pat. Nos. 4,501,058 and 4,501,059) and Oakes et al. (U.S. Pat. Nos. 5,200,189; 5,314,687; and 5,718,910) disclose peracid materials in a variety of end uses. Similarly, Cosentino et al. (U.S. Pat. No. 5,279,735) teach the use of peracid materials as a sterilant for hollow fiber membranes such as those used in kidney-dialysis procedures. Richter et al. (U.S. Pat. No. 5,436,008) teach unique peracid sanitizing materials having applicability for treating food-processing equipment.

Typical peracid materials include an equilibrium mixture of acetic acid, hydrogen peroxide, peroxyacetic acid, and a stabilizer. A stabilizer typically reduces the impact of divalent or trivalent metal ions on the decomposition of the active peroxygen species. Suitable stabilizers include a chelant or sequestrant.

Although peracid materials typically have a broad spectrum of antimicrobial properties, their activity against bacterial spores, fungal spores, and fungi can be less than desirable. Killing, inactivating, or otherwise reducing the active population of bacterial spores, fungal spores, and fungi on surfaces (e.g., especially food surfaces and food-contact surfaces, which are typically hard surfaces including metal, glass, composite materials, etc.) is a particularly difficult problem. In particular, bacterial spores have a unique chemical composition of spore layers that make them more resistant than vegetative bacteria to the antimicrobial effects of chemical and physical agents. Like bacterial spores, the unique chemical composition of fungal cells, especially mold spores, makes them more resistant to chemical and physical agents than other microorganisms.

A particularly difficult problem relates to microbiocidal treatment of bacterial spore-forming microorganisms of the Bacillus cereus group. Microorganisms of the Bacillus cereus group include Bacillus cereus, Bacillus mycoides, Bacillus anthracis, and Bacillus thuringiensis. These microorganisms share many phenotypical properties, have a high level of chromosomal sequence similarity, and are known enterotoxin producers.

Although all spore-forming microorganisms are problematic for microbiocidal treatments because they form spores, Bacillus cereus is one of the most problematic because Bacillus cereus has been identified as possessing increased resistance to germicidal chemicals used to decontaminate environmental surfaces. (See, e.g., Blakistone et al., Efficacy of Oxonia® Active Against Selected Sporeformers, Journal of Food Protection, Volume 62, pp. 262–267, reporting that Bacillus cereus was more tolerant to the effects of peroxyacetic acid germicides formulated using conventional parameters than all other spore-forming bacteria tested, including other Bacillus and Clostridium species.).

Bacillus cereus is a particularly well-established enterotoxin producer and food-borne pathogen. This organism is frequently diagnosed as a cause of gastrointestinal disorders and has been suggested to be the cause of several food-borne illness outbreaks. The organism is ubiquitous in nature, and as a consequence, is present in animal feed and fodder. Due to its rapid sporulating capacity, the organism easily survives in the environment and can survive intestinal passage in cows. The organism can contaminate raw milk via feces and soil, and Bacillus cereus can easily survive the pasteurization process.

Bacillus cereus is also known to cause serious human illness via environmental contamination. For example, Bacillus cereus is known to cause post-traumatic eye infections, which can cause visual impairment or loss of vision within 12–48 hours after infection.

A substantial need therefore exists for improving peracid materials so that they have greater antimicrobial activity toward bacterial spores and fungi and other microorganisms with resistance to germicidal materials, particularly activity against microorganisms of the Bacillus cereus group.

SUMMARY OF THE INVENTION

A common belief in the field of microbiocidal treatments is that peroxycarboxylic acid and hydrogen peroxide work cooperatively in microbiocidal treatments to reduce microbial populations. And it is generally believed that peroxyacetic acid and hydrogen peroxide at aqueous concentrations of about 1 to 10 weight percent can each have significant independent antimicrobial properties.

Yet according to this invention, hydrogen peroxide has surprisingly been found to facilitate the resistance of bacterial spores, particularly of the Bacillus cereus group, toward peracid material. Means to reduce peroxide induced resistance and increase efficacy is needed.

A composition of the invention is directed to reducing the concentration of hydrogen peroxide relative to a peroxycarboxylic acid from conventional concentrations to a level described herein. Reducing the hydrogen peroxide concentration relative to peroxycarboxylic acid provides a degree of antimicrobial properties that is surprising and unique in this technology.

A composition of the invention typically includes hydrogen peroxide, a carboxylic acid, and a peroxycarboxylic acid in which the ratio of peroxycarboxylic acid to hydrogen peroxide is at least 4:1, preferably at least 5:1, more preferably at least 6:1, and even more preferably at least 7:1. These ratios are expressed in parts by weight of peroxycarboxylic acid to each part by weight of hydrogen peroxide.

A composition of the invention typically has increased antimicrobial activity, particularly antisporicidal activity, as compared to peracid materials containing greater amounts of hydrogen peroxide relative to a peroxycarboxylic acid than a composition of the invention, when all conditions except for the hydrogen-peroxide amount are held constant.

In one embodiment, a concentrate composition includes hydrogen peroxide in an amount of between about 0.5 weight percent and about 80 weight percent; a carboxylic acid of the formula $R(COOH)_n$, in which R includes hydrogen, alkyl, alkenyl, alicyclic group, aryl, heteroaryl, or heterocyclic group, and n is 1, 2, or 3, the carboxylic acid being present in an amount of between about 5 weight percent and about 80 weight percent; and a peroxycarboxylic acid of the formula $R(COOOH)_n$, in which R includes hydrogen, alkyl, alkenyl, alicyclic group, aryl, heteroaryl, or heterocyclic group, and n is 1, 2, or 3, the peroxycarboxylic acid being present in an amount of between about 0.2 weight percent and about 30 weight percent, and the ratio of the peroxycarboxylic acid to hydrogen peroxide is at least 4:1.

In another embodiment, a use-solution composition includes hydrogen peroxide in an amount of up to 2500 ppm; a carboxylic acid of the formula $R(COOH)_n$, in which R includes hydrogen, alkyl, alkenyl, alicyclic group, aryl, heteroaryl, or heterocyclic group, and n is 1, 2, or 3, the carboxylic acid being present in an amount of between about 2 ppm and about 27000 ppm; and a peroxycarboxylic acid of the formula $R(COOOH)_n$, in which R includes hydrogen, alkyl, alkenyl, alicyclic group, aryl, heteroaryl, or heterocyclic group, and n is 1, 2, or 3, the peroxycarboxylic acid being present in an amount of between about 1 ppm and about 10000 ppm, and the ratio of the peroxycarboxylic acid to hydrogen peroxide is at least 4:1.

A composition of the invention can also contain additives such as, for example, a quaternary ammonium compound, a stabilizing agent, a hydrotrope, a surfactant, and/or another adjuvant to provide additional properties.

In one embodiment, a composition of the invention further includes a quaternary ammonium compound. In some instances, the sporicidal and fungicidal efficacy of a composition of the invention can be further improved by including a quaternary compound.

A method of the invention typically include contacting a substance with a composition of the invention to reduce microbial populations. This method is surprisingly effective for killing bacterial spores, particularly spore of the *Bacillus cereus* group.

In one embodiment, a method includes contacting a substance being contaminated with microorganisms of the *Bacillus cereus* group with a composition including a peroxycarboxylic acid and hydrogen peroxide in a ratio of a peroxycarboxylic acid to hydrogen peroxide of about 4:1 or greater, preferably about 5:1 or greater, more preferably about 6:1 or greater, and even more preferably about 7:1 or greater.

Another method of the invention is directed to desirably reducing the concentration of hydrogen peroxide relative to the concentration of a peroxycarboxylic acid in a composition of the invention by, for example, reaction with a catalytic surface, reaction with a chemical agent, or application of other chemical techniques.

In one embodiment, the concentration can be desirably reduced relative to the concentration of a peroxycarboxylic acid by controlling the equilibrium reaction between hydrogen peroxide and a carboxylic acid.

In another embodiment, the concentration can be desirably reduced relative to the concentration of a peroxycarboxylic acid by exposing a composition of the invention to a hydrogen peroxide-destroying agent such as catalase.

DETAILED DESCRIPTION OF THE INVENTION

Figure 1:
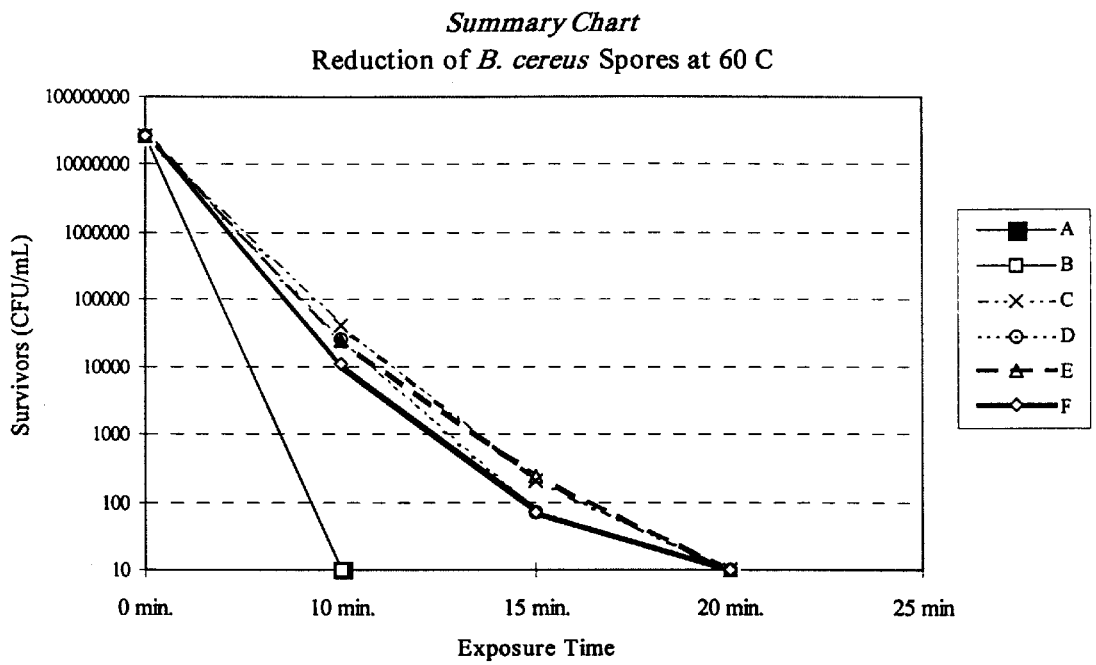
FIG. 1 illustrates the reduction of *Bacillus cereus* spores by modified and modified compositions of the invention at 60° C. after variable exposure time to a series of peroxyacetic-acid-containing compositions.

The invention is directed to compositions suitable for use in a microbiocidal treatment of a variety of substances and to methods of microbiocidal treatment of a variety of substances.

A composition of the invention is useful against microorganisms, including vegetative bacteria, spore, bacterial spore, fungi, fungal spores (e.g. yeasts, molds) viruses, parasites, etc. A composition of the invention is particularly useful against microorganisms of the *Bacillus cereus* group and more particularly useful against spores of the *Bacillus cereus* group.

A microbiocidal treatment includes any treatment of a variety of substances directed against reducing, eliminating, or inactivating microbial contaminants on a surface of a treated substance. A microbiocidal treatment can provide antimicrobial activity such as antibacterial, antifungal, antiviral, or antiparasitic activity. Such antimicrobial activity includes activity that can be effective against the deterioration of a substance, activity that can contribute to human or animal contaminant-related illnesses, activity that can reduce the storage time of a substance, etc.

The term "reducing" includes desirably reducing the number of microorganisms on a treated substance. A desirable amount of reduction in microbial number can be based on industry standards, government regulations, etc, but must be significant, in that conventional statistical methods confirm that the reduction quantity is statistically significant. Typically a desirable amount of reduction is calculated in terms of a $\log_{10}$ reduction. A composition of the invention generally provides antimicrobial activity of at least a fraction of a $\log_{10}$ reduction greater than conventional compositions for microbiocidal treatments when all conditions are identical except for the relative amounts of peroxycarboxylic acid and hydrogen peroxide. That is, when making such a comparison, the only variation between the microbiocidal treatment of the invention and the conventional microbiocidal treatment is that a conventional composition has a greater amount of hydrogen peroxide relative to peroxycarboxylic acid than a composition of the invention.

Although this invention is not limited to any particular theory, one theory suggests that a microorganism, including spores, may have resistance to microbiocidal treatments using an antimicrobial material because certain components may block others from acting against the microorganism or because certain components may cause a microorganism to adopt a defensive metabolism against the antimicrobial material. In particular, for peracid materials, one theory suggests that in some microorganisms, hydrogen peroxide triggers a resistance mechanism against the peracid material. Thus, a composition of the invention may have improved antimicrobial activity, as compared to conventional compositions, because the peroxycarboxylic-acid resistance mechanism of targeted microorganisms, particularly microorganisms of the *Bacillus cereus* group, is less likely triggered by a composition of the invention.

A composition of the invention is suitable for treating a variety of substances in a variety of environments. A composition of the invention can be used in any environment where it can be desirable to reduce microbial contamination, particularly microbial contamination arising from microorganisms of the *Bacillus cereus* group, for example, the health-care industry (e.g., animal hospitals, human hospitals, animal clinics, human clinics, nursing homes, day-care facilities for children or senior citizens, etc.), the food industry (e.g., restaurants, food-processing plants, food-storage plants, grocery stores, etc.), the hospitality industry (e.g., hotels, motels, resorts, cruise ships, etc.), the education industry (e.g., schools and universities), the water treatment industry, cooling towers flumes, pools, spas, etc.

A composition of the invention can be used to treat a variety of substances for which it can be desirable to reduce microbial contamination, particularly microbial contamination arising from microorganisms of the *Bacillus cereus* group, for example, general-premise surfaces (e.g., floors, walls, ceilings, exterior of furniture, etc.), specific-equipment surfaces (e.g., hard surfaces, manufacturing equipment, processing equipment, etc.), textiles (e.g., cottons, wools, silks, synthetic fabrics such as polyesters, polyolefins, and acrylics, blends of fibers such as cotton-polyester blends, etc.), wood and cellulose-based systems (e.g., paper), soil, animal carcasses (e.g., hide, meat, hair, feathers, etc.), foodstuffs (e.g., fruits, vegetables, nuts, meats, etc.), and water.

A composition of the invention can be formulated in a variety of concentrations depending on, for example, transport costs, industry standard, application, etc. A composition of the invention can be formulated as, for example, a concentrate composition, a use solution, a two-part system, etc.

A concentrate composition can be used without dilution in some instances. But a concentrate composition is typically diluted with a diluent such as, for example, water prior to use.

A use solution can be prepared by diluting a concentrate composition in a diluent such as, for example, water. Typically a use solution of the invention is used in a microbiocidal treatment of a substrate, particularly in a microbiocidal treatment of a textile.

A multiple-part system for a composition of the invention includes providing the components in multiple parts, for example, hydrogen peroxide, carboxylic acid, and peroxycarboxylic acid in one part and one or more additives in one or more additional parts. The parts can be combined to produce a concentrate composition of the invention or a use solution of the invention. A multiple-part system can be particularly advantageous when one or more additives may adversely affect the antimicrobial activity of a composition of the invention. A multiple-part system allows for such additives to be added to a composition of the invention immediately prior to a microbiocidal treatment.

Composition

A composition of the invention includes an effective reduced amount of hydrogen peroxide, an effective amount of carboxylic acid, and an effective amount of peroxycarboxylic acid to produce the effective chemical species and reduce microbial and spore populations. A composition of the invention can also include additives such as, for example, a quaternary ammonium compound, a stabilizing agent, a hydrotrope, a surfactant, an adjuvant, etc.

A composition of the invention includes an equilibrium mixture of a peroxycarboxylic acid, hydrogen peroxide, and a carboxylic acid resulting from an acid-catalyzed equilibrium reaction between hydrogen peroxide and a carboxylic acid to form a peroxycarboxylic acid.

For an acid-catalyzed equilibrium reaction, a peroxycarboxylic acid, hydrogen peroxide, and a carboxylic acid move toward an equilibrium in which the relative proportions of each constituent depends on the relative proportions and concentrations of the carboxylic acid and the hydrogen peroxide used as starting materials.

As the mixture approaches equilibrium, the proportion of peroxycarboxylic acid increases until a maximum is obtained at equilibrium. The rate at which the composition moves toward equilibrium can depend on the concentrations of the reactants, the prevailing temperature, and/or a concentration of a catalyst such as, for example, a strong organic or inorganic acid (e.g., phosphoric acid, phosphonic acid, sulfuric acid, sulfonic acid, etc.). By controlling the acid-catalyzed equilibrium reaction by, for example, controlling the concentrations of the carboxylic acid, the hydrogen peroxide, and water, the ratios of peroxycarboxylic acid and hydrogen peroxide in a composition of the invention can be controlled. Preferably the concentration of peroxycarboxylic acid is maximized and the concentration of hydrogen peroxide is minimized relative to each other.

Hydrogen Peroxide

A composition of the invention includes hydrogen peroxide. Hydrogen peroxide includes any aqueous solution of hydrogen peroxide and solutions of alkali-metal hydrogen peroxides, alkali salts of percarbonate and persulfate, and organic peroxides. Organic peroxides include solutions of hydrogen peroxide that include, for example, dicumyl peroxide, dialkyl peroxides, urea peroxide, etc. as the basis of the solution of the hydrogen peroxide. Preferably the hydrogen peroxide source is an aqueous solution of hydrogen peroxide.

Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid.

Another advantage of hydrogen peroxide is that it decomposes into water and oxygen. Thus, after a composition of the invention is used for a microbiocidal treatment of a substance, the combination of the peroxycarboxylic acid and hydrogen peroxide decomposes into the corresponding carboxylic acid, water, and oxygen.

For example, in one embodiment, the composition of the invention includes peroxyacetic acid and hydrogen peroxide. After being used for a microbiocidal treatment, peroxyacetic acid and hydrogen peroxide decompose to acetic acid, water, and oxygen. It is advantageous to have these decomposition products because they are generally compatible with substances being treated. For example, the decomposition products are generally compatible with metallic substance (e.g., substantially noncorrosive) and compatible with food products (e.g., does not substantially alter the color, flavor, or nutritional value of a food product). And the decomposition products are generally innocuous to incidental contact with humans and are environmentally friendly.

A composition of the invention typically includes hydrogen peroxide in an amount effective for maintaining the equilibrium between a carboxylic acid, hydrogen peroxide, and a peroxycarboxylic acid. The amount of hydrogen peroxide should not exceed an amount that would adversely affect the antimicrobial activity of a composition of the invention. Moreover, a composition of the invention preferably contains hydrogen peroxide at a concentration as close to zero as possible. That is, the concentration of hydrogen peroxide is minimized.

One advantage of minimizing the concentration of hydrogen peroxide is that antimicrobial activity of a composition of the invention is improved as compared to conventional compositions.

Yet an excess of hydrogen peroxide, however slight, is typically maintained within the starting composition (i.e., the reaction of carboxylic acid with hydrogen peroxide) to achieve an equilibrium yield of peroxycarboxylic acid within a reasonable time frame. A reasonable time frame includes, for example, less than 21 days, preferably less than 14 days, and more preferably less than 7 days. As a result, a composition of the invention typically includes a residual amount of hydrogen peroxide greater than zero. Storage stability can also limit the minimal amount of hydrogen peroxide that can be present. A composition of the invention is preferably storage stable for at least six months, more preferably at least twelve months, and even more preferably at least twenty-four months. "Storage stability" as used herein refers to maintaining at least 90 weight percent, preferably 95 weight percent of the original equilibrium concentration of hydrogen peroxide, a carboxylic acid, and a peroxycarboxylic acid during storage of the composition at ambient temperature.

In one embodiment, the concentration of hydrogen peroxide can be reduced to about zero active hydrogen peroxide by reaction with a hydrogen-peroxide destroying enzymatic agent such as, for example, an enzyme (e.g., catalase, peroxidase, etc.), a metal (e.g., platinum metal), etc. But reducing hydrogen peroxide by this method likely is impractical for industrial use because of prohibitive cost.

An enzymatic agent can be used to destroy the activity of hydrogen peroxide by, for example, arranging the enzymatic agent in a small fixed bed reactor or column through which the composition of the invention passes within 4 hours prior to use. Although such a process can cause the remaining peroxycarboxylic acid to shift toward starting materials and seek a new equilibrium, dilution should prolong the LeChatelier effect and not substantially reduce antimicrobial activity of the composition of the invention.

An alternative but less preferred method for using an enzymatic agent to destroy the activity of hydrogen peroxide is to directly add the enzymatic agent to a composition of the invention prior to use.

Hydrogen peroxide can typically be present in a use solution in an amount of up to about 2500 ppm, preferably between about 3 ppm and about 1850 ppm, and more preferably between about 6 ppm and about 1250 ppm. The term "ppm" is defined as parts per million and refers to amounts once the composition has reached equilibrium.

Alternatively, hydrogen peroxide can be present in a concentrate composition intended for dilution at one ounce concentrate composition to less than about 2 gallons up to about 15 gallons and more, preferably between about 4 gallons and about 10 gallons, water in an amount of between about 0.2 weight percent and about 6 weight percent, preferably between about 0.5 weight percent and about 5 weight percent, and more preferably between about 0.8 weight percent and about 4 weight percent.

The term "weight percent" as used herein refers to a weight/weight percent of 100% active ingredients once the composition has reached equilibrium.

One skilled in the art will appreciate that amounts of components in a concentrate composition will vary depending on the end dilution desirable. The desirable end dilution can depend on industry standard, transport costs, application, etc. Thus, a concentrate composition may be diluted in more than 15 gallons of water.

Carboxylic Acid

A composition of the invention also includes a carboxylic acid. A carboxylic acid includes any compound of the formula R—(COOH)n in which R can be hydrogen, alkyl, alkenyl, alicyclic group, aryl, heteroaryl, or heterocyclic group, and n is 1, 2, or 3. Preferably R includes hydrogen, alkyl, or alkenyl.

The term "alkyl" includes a straight or branched saturated aliphatic hydrocarbon chain having from 1 to 12 carbon atoms, such as, for example, methyl, ethyl, propyl, isopropyl (1-methylethyl), butyl, tert-butyl (1,1-dimethylethyl), and the like.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like.

The above alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

The term "alicyclic" includes any cyclic hydrocarbyl containing from 3 to 8 carbon atoms. Examples of suitable alicyclic groups include cyclopropanyl, cyclobutanyl, cyclopentanyl, etc.

The term "heterocyclic" includes any cyclic hydrocarbyl containing from 3 to 8 carbon atoms that is interrupted by a heteroatom, such as, for example, a nitrogen, sulfur, or oxygen atom. Examples of suitable heterocyclic groups include groups derived form tetrahydrofurans, furans, thiophenes, pyrrolidines, piperidines, pyridines, pyrrols, picoline, coumaline, etc.

Alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy.

The term "aryl" includes aromatic hydrocarbyl, including fused aromatic rings, such as, for example, phenyl and naphthyl.

The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc.

The term "heteroaryl" also includes fused rings in which at least one ring is aromatic, such as, for example, indolyl, purinyl, benzofuryl, etc.

Aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Examples of suitable carboxylic acids include a variety monocarboxylic acids, dicarboxylic acids, and tricarboxylic acids.

Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc.

Dicarboxylic acids include, for example, adipic acid, fumaric acid, glutaric acid, maleic acid, succinic acid, malic acid, tartaric acid, etc.

Tricarboxylic acids include, for example, citric acid, trimellitic acid, isocitric acid, agaicic acid, etc.

A carboxylic acid suitable for use in a composition of the invention can be selected for its solubility, cost, approval as food additive, odor, purity, etc.

A particularly useful carboxylic acid for a composition of the invention includes a carboxylic acid that is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. These carboxylic acids can also be useful because water-soluble carboxylic acids can be food additives such as formic acid, acetic acid, lactic acid, citric acid, tartaric acid, etc.

Preferably a composition of the invention includes acetic acid, octanoic acid, or propionic acid, lactic acid, heptanoic acid, octanoic acid, or nonanoic acid.

A composition of the invention can include a carboxylic acid in an amount effective for maintaining the equilibrium between a carboxylic acid, hydrogen peroxide, and a peroxycarboxylic acid. A carboxylic acid can typically be present in a use solution in an amount of between about 2 ppm and about 27000 ppm, preferably between about 100 ppm and about 21000 ppm, and more preferably between about 200 ppm and about 15000 ppm.

Alternatively, a carboxylic acid can be present in a concentrate composition intended for dilution at one ounce concentrate composition to between about 2 gallons and about 15 gallons, preferably between about 4 gallons and about 10 gallons, water in an amount of between about 0.5 weight percent and about 80 weight percent, preferably between about 10 weight percent and about 70 weight percent, and more preferably between about 15 weight percent and about 60 weight percent.

In one embodiment, a concentrate composition intended for dilution at 1 ounce to between about 2 gallons and about 15 gallons, preferably between about 4 gallons, and about 10 gallons, more preferably about 6 gallons, water includes a carboxylic acid in which R includes alkyl of 1–4 carbon atoms in an amount of between about 0.5 weight percent and about 25 weight percent, preferably between about 1 weight percent and about 20 weight percent, and more preferably between about 2 weight percent and about 15 weight percent. In another embodiment, a concentrate composition further includes a carboxylic acid in which R includes alkyl of 14 carbon atoms.

Peroxycarboxylic Acid

A composition of the invention also includes a peroxycarboxylic acid. A peroxycarboxylic acid is also known in the art as a percarboxylic acid, a peroxyacid, and a peracid.

A peroxycarboxylic acid includes any compound of the formula R—(COOOH)$_n$ in which R can be hydrogen, alkyl, alkenyl, alicyclic group, aryl, heteroaryl, or heterocyclic group, and n is 1, 2, or 3. Preferably R includes hydrogen, alkyl, or alkenyl.

The terms "alkyl," "alkenyl," "alicyclic group," "aryl," "heteroaryl," and "heterocyclic group" are as defined above.

Peroxycarboxylic acids useful in this invention include any peroxycarboxylic acid that can be prepared from the acid-catalyzed equilibrium reaction between a carboxylic acid described above and hydrogen peroxide described above. Preferably a composition of the invention includes peroxyacetic acid, peroxyoctanoic acid, or peroxypropionic acid, peroxylactic acid, peroxyheptanoic acid, peroxyoctanoic acid, or peroxynonanoic acid.

Although less preferred, a peroxycarboxylic acid can also be prepared by the auto-oxidation of aldehydes or by the reaction of hydrogen peroxide with an acid chloride, acid hydride, carboxylic acid anhydride, or sodium alcoholate.

In some embodiments, a peroxycarboxylic acid includes at least one water-soluble peroxycarboxylic acid in which R includes alkyl of 1–4 carbon atoms. For example, in one embodiment, a peroxycarboxylic acid includes peroxyacetic acid. In another embodiment, a peroxycarboxylic acid has R that is an alkyl of 1–4 carbon atoms substituted with hydroxy.

Methods of preparing peroxyacetic acid are known to those of skill in the art including those disclosed in U.S. Pat. No. 2,833,813, which is incorporated herein by reference.

One advantage of using a peroxycarboxylic acid in which R includes alkyl of 1–4 carbon atoms is that such peroxycarboxylic acids traditionally have a lower pKa than peroxycarboxylic acids having R that is alkyl with more than 4 carbon atoms. This lower pKa can favor a faster rate of peroxycarboxylic acid equilibrium and can be effective for providing a composition of the invention with, for example, acidic pH, which can be advantageous for improved limescale and/or soil removal.

In other embodiments, a peroxycarboxylic acid includes at least one peroxycarboxylic acid of limited water solubility in which R includes alkyl of 5–12 carbon atoms and at least one water-soluble peroxycarboxylic acid in which R includes alkyl of 1–4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid.

One advantage of combining a water-soluble carboxylic acid or peroxycarboxylic acid with a carboxylic acid or peroxycarboxylic acid having limited water solubility is that the water-soluble carboxylic acid or peroxycarboxylic acid can provide a hydrotropic effect upon less water soluble carboxylic and peroxycarboxylic acids, which can facilitate uniform dispersion and/or consequent physical stability within the composition.

Another advantage of this combination of peroxycarboxylic acids is that it can provide a composition of the invention with desirable antimicrobial activity in the presence of high organic soil loads such as, for example, in the treatment of animal carcasses, body-fluid spills in hospitals, laundry from hospitals and hotels, etc.

A composition of the invention can include a peroxycarboxylic acid, or mixtures thereof, in an amount effective for maintaining the equilibrium between carboxylic acid, hydrogen peroxide, and peroxycarboxylic acid and for providing effective antimicrobial activity. A peroxycarboxylic acid can typically be present in a use solution in an amount of between about 1 ppm and about 30000, 2 ppm and about 27000 ppm, preferably between about 100 ppm and 21000 ppm, and more preferably between about 200 ppm and about 15000 ppm.

Alternatively, peroxycarboxylic acid can be present in a concentrate composition intended for dilution at one ounce concentrate composition to between about 2 gallons and about 15 gallons, preferably between about 4 gallons and about 10 gallons, more preferably about 6 gallons, water in an amount of between about 0.2 weight percent and about 30 weight percent, preferably between about 2.5 weight percent and about 25 weight percent, and more preferably between about 4 weight percent and about 20 weight percent.

A composition of the invention generally includes peroxycarboxylic acid and hydrogen peroxide in a ratio of at least 4:1, preferably at least 5:1, preferably at least 6:1, and even more preferably at least 7:1. This ratio is determined with equilibrium amounts of components, and the amounts used can be based on weight percent or parts per million.

Additional Components

A composition of the invention can include additives such as, for example, a quaternary ammonium compound, a stabilizing agent, a hydrotrope, a surfactant, and an adjuvant. Additives can enhance the antimicrobial/antifungal activity of a composition of the invention and/or can provide a composition of the invention with additional qualities such as, for example, cleaning action, sensory appeal, etc.

Any additive included in a composition of the invention should be compatible with the other components in the composition in the long term, for example, at least 6 months, preferably 12 months, and more preferably 2 years, for single product compositions or in the short term for multiple-component cooperative compositions admixed at time of use.

Quaternary Ammonium Compound

A composition of the invention can include a quaternary ammonium compound. A quaternary ammonium compound can be effective for enhancing the antimicrobial/antifungal activity of a composition of the invention.

Any quaternary ammonium compound with antimicrobial activity can be used in the composition of the invention. A quaternary ammonium compound suitable for use is with a composition of the invention includes a compound of the formula $(NR_1R_2R_3R_4)^+X^-$ in which $R_1$–$R_4$ are independently alkyl, alkenyl, aryl, or heteroaryl, and $X^-$ is an anionic counterion.

The terms "alkyl," "alkenyl," "aryl," and "heteroaryl" are as defined above except where indicated to the contrary.

The term "anionic counterion" includes any ion that can form a salt with quaternary ammonium.

Examples of suitable anionic counterions include chloride, propionates, methosulphates, saccharinates, ethosulphates, hydroxides, acetates, phosphates, and nitrates. Preferably the anionic counterion is chloride.

When using quaternary ammonium compounds having a chloride counterion, the quaternary ammonium chloride should be mixed with a composition of the invention just prior to use for antimicrobial activity because the chloride ion can cause rapid degradation of active oxygen species.

Useful quaternary ammonium compounds include N-alkyl dimethyl benzyl ammonium, N-alkyl dimethyl ethyl benzyl ammonium, di-n-alkyl dimethyl ammonium and di-n-alkyl methyl benzyl ammonium salts or mixtures thereof, in which alkyl contains from 1 to 20 carbon atoms in each alkyl group or is interrupted by oxygen to form an oxyalkyl from 1 to 8 carbon atoms.

Other quaternary ammonium compounds suitable for use in a composition of the invention include di-n-alkyl dimethyl ammonium chlorides such as didecyl dimethyl ammonium chloride sold under the trade name Bardac™ 2250 or 2280 available from Lonza, Inc. (Fair Lawn, N.J.), dioctyl dimethyl ammonium chloride sold under the trade name Bardac™ LF and Bardac™ LF-80 and octyl decyl dimethyl ammonium chloride sold in mixture with didecyl and dioctyl dimethyl ammonium chlorides under the trade to name Bardac™ 2050 and 2080.

A composition of the invention can include a quaternary ammonium compound in an amount effective for enhancing the antimicrobial activity of a composition of the invention. A quaternary ammonium compound can be present in a use solution in an amount of up to about 200 ppm, preferably between about 4 ppm and about 100 ppm, and more preferably between about 10 ppm and about 50 ppm.

Alternatively, a quaternary ammonium compound can be present in a concentrate composition intended for dilution at one ounce concentrate composition to between about 2 gallons and about 15 gallons, preferably between about 4 gallons and about 10 gallons, more preferably about 6 gallons, water in an amount of up to about 10 weight percent, preferably between about 0.08 weight percent and about 7 weight percent, and more preferably between about 0.15 weight percent and about 4 weight percent.

Stabilizing Agents

A composition of the invention can also include a stabilizing agent to reduce the likelihood of that the peroxygen components, such as a peroxycarboxylic acid or hydrogen peroxide in a composition of the invention, decomposing to oxygen and an unoxidized species.

Although this invention is not limited by any one theory, one theory indicates that aqueous solutions containing peroxycarboxylic acids can decompose in three ways: (1) spontaneous decomposition to yield the corresponding carboxylic acid and oxygen; (2) hydrolysis under strongly acidic or basic conditions to give the carboxylic acid and hydrogen peroxide; and (3) catalytic decomposition by heavy metals and their salts to yield mainly carbon dioxide, oxygen, and the carboxylic acid. Catalytic decomposition can be of particular concern because starting materials, additives, and/or equipment with which the composition comes into contact can provide impurities to a composition of the invention.

A stabilizing agent can be added to the composition of the invention to prevent or retard this catalytic effect within the composition and during use to enhance antimicrobial activity. It will be recognized that compositions that are prepared and diluted just prior to use are less likely to have decomposition problems than compositions prepared for long-term storage, for example, up to about 6 months.

Any compound that can reduce the likelihood of decomposition of the composition of the invention can be used as a stabilizing agent. Typically stabilizing agents sequester metals to protect against decomposition. Thus, any compound that can sequester metals can be used as a stabilizing agent in a composition of the invention.

Examples of suitable stabilizing agents include polycarboxylic acids (e.g., dipicolinic acid, ethylenediaminetetraacetic acid, or citric acid), soluble salts of phosphates that may take the form of simple monomeric species or of condensed linear polyphosphates or cyclic metaphosphates, and the like.

Other examples of suitable stabilizing agents include organophosphonic acids and their salts. Organophosphonic acids and their salts can contain other functional groups such as hydroxy or amino. These are exemplified in compounds such as 1-hydroxyethylidene-1,1-diphosphonic acid (Dequest® 2010, Monsanto, St. Louis, Mo.) and poly (methyleneamino)-phosphonic acids (Briquest®, Uniqema, Wilmington, Del.) such phosphoric as amino (trimethylenephosphonic acid) and diethylenetriaminepenta (methylenephosphonic acid).

Preferably a stabilizing agent includes a phosphonic acid. Phosphonic acid can serve as a strong acid catalyst to increase the rate of peroxycarboxylic acid formation during the equilibrium reaction. In one embodiment, a composition of the invention includes Dequest® 2010.

A composition of the invention can include a stabilizing agent in a concentration effective to provide protection against decomposition of components of a composition of the invention.

A stabilizing agent can be present in a use solution in an amount of up to about 150 ppm, preferably between about 2 ppm and about 100 ppm, and more preferably between about 3 ppm and about 50 ppm.

Alternatively, a stabilizing agent can be present in a concentrate composition intended for dilution at one ounce concentrate composition to between about 2 gallons and about 15 gallons, preferably between about 4 gallons and about 10 gallons, more preferably about 6 gallons, water in an amount of up to about 10 weight percent, preferably between about 0.1 weight percent and about 5 weight percent, and more preferably between about 0.2 weight percent and about 3 weight percent.

In one embodiment, a composition of the invention includes acetic acid in an amount of between about 60 weight percent and about 70 weight percent, hydrogen peroxide in an amount of between about 1.0 weight percent and about 2.5 weight percent, peroxyacetic acid in an amount of between about 10 weight percent and about 15 weight percent, and a stabilizing agent in an amount of between about 0.1 weight percent and about 1 weight percent. Preferably the stabilizing agent is Dequest® 2010.

In still another embodiment, a composition of the invention includes acetic acid in an amount of between about 64 weight percent and about 66 weight percent, hydrogen peroxide in an amount of between about 1.5 weight percent and about 2 weight percent, peroxyacetic acid in an amount of between about 11.5 weight percent and about 13.5 weight percent, and a stabilizing agent in an amount of between about 0.5 weight percent and about 0.7 weight percent. Preferably the ratio of peroxyacetic acid to hydrogen peroxide is about 7:1.

Hydrotropes

A composition of the invention can also include a hydrotrope. A hydrotrope can increase the miscibility, solubility, or phase stability of organic and inorganic materials in aqueous solution by physicochemical association. A hydrotrope can also facilitate physical stability and/or homogenicity of a composition of the invention in a concentrate and can facilitate solubilization of the same ingredients in a use solution.

A hydrotrope can be particularly useful in a composition of the invention when mixtures of precursive carboxylic acids are used and one or more have limited water solubility. For example, hydrotropes can be particularly useful for compositions containing peroxycarboxylic acids having R that is $C_{5-2}$ alkyl.

A hydrotrope includes any compound suitable for solubilizing intermediaries.

Examples of suitable hydrotropes include xylene-, cumene-, toluene sulfonic acids, alkyl benzene sulfonic acids, n-octane sulfonic acids, naphthalenesulfonic acids, alkyl- and dialkyl naphthalenesulfonic acids, diphenyletherdisulfonic acids, or their alkali metal salts.

Other examples include phosphate esters, amine oxides, and polyols containing only carbon, hydrogen, and oxygen atoms and containing from about 2 to about 6 hydroxy groups. Polyol examples include 1,2-propanediol, 1,2-butanediol, hexylene glycol, glyerol, sorbitol, mannitol, and glucose.

Concentrations of a hydrotrope suitable for use in a composition of the invention can vary according to the concentration of carboxylic and peroxycarboxylic acids and their respective solubilities within the starting composition.

A hydrotrope can be present in a use solution in an amount of up to about 3500 ppm, preferably between about 10 ppm and about 2500 ppm, and more preferably between about 30 ppm and about 1500 ppm.

Alternatively, a hydrotrope can be present in a concentrate composition intended for dilution at one ounce concentrate composition to between about 2 gallons and about 15 gallons, preferably between about 4 gallons and about 10 gallons, more preferably about 6 gallons, water in an amount of up to about 20 weight percent, preferably between about 1 weight percent and about 15 weight percent, and more preferably between about 3 weight percent and about 10 weight percent.

Surfactants

A composition of the invention can also include a surfactant. A surfactant can include any compound suitable for affecting the foaming, detergency, and/or wetting of a composition of the invention.

Examples of surfactants suitable for use with a composition of the invention include water-soluble or water-dispersible nonionic, semi-polar nonionic, cationic or amphoteric surface-active agents. One skilled in the art will understand that anionic surfactants can be used but will recognize that the inclusion of quaternary ammonium compounds in the composition of the invention should be limited or prevented because these compounds can have ion-pair incompatibility.

In one embodiment, a composition of the invention includes a nonionic surfactant. Some advantages of a nonionic surfactant is that there is comprehensive commercial selection and nonionic surfactants have a desirable detersive effect (i.e., surface wetting, soil penetration, and soil removal and suspension from the surface being cleaned and disinfected).

Examples of nonionic surfactants suitable for a composition of the invention include a surfactant with ethylene oxide moieties, propylene oxide moieties, or mixtures thereof, and surfactants with ethylene oxide-propylene oxide moieties in either heteric or block formation. Additionally useful in the present invention are nonionic surfactants that include alkyl ethylene oxide compounds, alkyl propylene oxide compounds, and alkyl ethylene oxide-propylene oxide compounds, and alkyl ethylene oxide-propylene oxide compounds where the ethylene oxide propylene oxide moiety is either in heteric or block formation.

Further useful nonionic surfactants in a composition of the invention include nonionic surfactants having any mixture or combination of ethylene oxide-propylene oxide moieties linked to an alkyl chain where the ethylene oxide and propylene oxide moieties may be in any randomized or ordered pattern and of any specific length. Other nonionic surfactants useful in a composition of the invention include a surfactant having randomized sections of block and heteric ethylene oxide-propylene oxide. Nonionic moieties can be capped with a benzyl, alkoxy, or short-chain alkyl grouping.

A surfactant can be present in a use solution in an amount of up to about 2000 ppm, preferably between about 5 ppm and about 1000 ppm, and more preferably between about 10 ppm and about 500 ppm.

Alternatively, a surfactant can be present in a concentrate composition intended for dilution at one ounce concentrate composition to between about 2 gallons and about 15 gallons, preferably between about 4 gallons and about 10 gallons, more preferably about 6 gallons, water in an amount of up to about 15 weight percent, preferably between about 0.01 weight percent and about 10 weight percent, and more preferably between about 0.1 weight percent and about 5 weight percent.

Adjuvants

A composition of the invention can also contain any number of other constituents that are known to those of skill in the art and that may facilitate the microbiocidal treatment of the invention.

Other constituents that may be useful in compositions of the invention include strong inorganic acids (e.g., phosphoric, nitric, sulfuric, and sulfamic acids) and strong organosulfonic acids (e.g., decylsulfonic, dodecylsulfonic, toluene sulfonic, and methylsulfonic acids). Strong inorganic or organosulfonic acids may be used as catalysts to speed equilibration of the compositions and/or to serve as strong acidulants for dissolving inorganic and inorganic-organic soil matrices such as hard water films, milk-stone, and beer-stone from surfaces.

Other constituents that can be useful for compositions of the invention include manufacturing aids such as defoamers, corrosion inhibitors, rheology modifiers, dye and pigment colorants, and fragrances.

Tables A, and B illustrate ingredients and ranges for compositions of the invention.

Table A illustrates the useful, preferred, and more preferred ranges of a carboxylic acid, hydrogen peroxide, and a peroxycarboxylic acid included in a composition of the invention intended as a concentrate composition. Table 1 also illustrates useful, preferred, and more preferred ranges of a quaternary ammonium compound and a stabilizing agent, which can be included in a composition of the invention.

Table A illustrates the useful, preferred, and more preferred ranges of a carboxylic acid, hydrogen peroxide, and a peroxycarboxylic acid included in a composition of the invention intended as a concentrate composition. Table A also illustrates useful, preferred, and more preferred ranges of a quaternary ammonium compound, a hydrotrope, a surfactant, and a stabilizing agent, which can be included in a composition of the invention.

A hydrotrope can be particularly useful in a composition of the invention containing a less water-miscible carboxylic acid.

TABLE A

Range of Ingredients for a Composition
of the Invention Intended as a Concentrate

| | Concentration (weight percent)** | | |
|---|---|---|---|
| *Ingredients | Useful | Preferred | More Preferred |
| Carboxylic Acid | 0.5–80 | 10–70 | 15–60 |
| Hydrogen Peroxide | 0.2–6 | 0.5–5 | 0.8–4 |
| Peroxycarboxylic Acid | 0.2–30 | 2.5–25 | 4–20 |
| Quaternary Ammonium Compound | 0–10 | 0.08–7 | 0.15–4 |
| Stabilizing Agent | 0–10 | 0.1–5 | 0.2–3 |
| Hydrotrope | 0–20 | 1–15 | 3–10 |
| Surfactant | 0–15 | 0.01–10 | 0.01–5 |
| Water | Balance | Balance | Balance |
| TOTAL: | 100% | 100% | 100% |

*All ingredients are listed as 100% active.
**Weight percents are post-equilibrium concentrations.

Table B illustrates the useful, preferred, and more preferred ranges of a carboxylic acid, hydrogen peroxide, and a peroxycarboxylic acid included in a composition of the invention intended as a use solution. Table 3 also illustrates useful, preferred, and more preferred ranges of a quaternary ammonium compound, a hydrotrope, a surfactant, and a stabilizing agent, which can be included in a composition of the invention.

TABLE B

Range of Ingredients for a Composition
of the Invention Intended as a Use Solution

| | Concentration (ppm)** | | |
|---|---|---|---|
| *Ingredients | Useful | Preferred | More Preferred |
| Carboxylic Acid | 2–27000 | 100–21000 | 200–15000 |
| Hydrogen Peroxide | 0–2500 | 3–1850 | 6–1250 |
| Peroxycarboxylic Acid | 1–10000 | 50–7500 | 100–5000 |
| Quaternary Ammonium Compound. | 0–200 | 4–100 | 10–50 |
| Stabilizing Agent | 0–150 | 2–100 | 3–50 |
| Hydrotrope | 0–3500 | 10–2500 | 30–1500 |
| Surfactant | 0–2000 | 5–1000 | 10–500 |
| Water | Balance | Balance | Balance |

*All ingredients are listed as 100% active.
**PPM's (parts per million) are post equilibrium concentrations.

One advantage of a composition of the invention is that the composition can include reduced amounts of hydrogen peroxide relative to peroxycarboxylic acid when compared to known compositions. This allows for compositions of the invention to have enhanced antimicrobial activity against particularly resistant bacterial spores, for example, spores of the Bacillus cereus group. That is, compositions of the invention have improved antimicrobial activity as compared to known compositions having peroxycarboxylic acid and hydrogen peroxide in a ratio of peroxycarboxylic acid to hydrogen peroxide of less than 4:1 such as, for example, 3:1. For such known compositions, this means that the amount of hydrogen peroxide is greater relative to the amount of peroxycarboxylic acid when compared to a composition of the invention. The term "improved antimicrobial activity" includes at least a fraction of a $\log_{10}$ greater as defined above.

Methods of Use

Methods of the invention are directed to microbiocidal treatment of a variety of substances. Microbiocidal treatment of a substance includes contacting a substance with a composition of the invention.

A composition of the invention is suitable for treating a variety of substances in a variety of environments. A composition of the invention can be used in any environment where it can be desirable to reduce microbial contamination, particularly microbial contamination arising from microorganisms of the Bacillus cereus group, for example, the health-care industry (e.g., animal hospitals, human hospitals, animal clinics, human clinics, nursing homes, day-care facilities for children or senior citizens, etc.), the food industry (e.g., restaurants, food-processing plants, food-storage plants, grocery stores, etc.), the hospitality industry (e.g., hotels, motels, resorts, cruise ships, etc.), the education industry (e.g., schools and universities), etc.

A composition of the invention can be used to treat a variety of substances for which it can be desirable to reduce microbial contamination, particularly microbial contamination arising from microorganisms of the Bacillus cereus group, for example, general-premise surfaces (e.g., floors, walls, ceilings, exterior of furniture, etc.), specific-equipment surfaces (e.g., hard surfaces, manufacturing equipment, processing equipment, etc.), textiles (e.g., cottons, wools, silks, synthetic fabrics such as polyesters, polyolefins, and acrylics, fiber blends such as cotton-polyester, etc.), wood and cellulose-based systems (e.g., paper), soil, animal carcasses (e.g., hide, meat, hair, feathers, etc.), foodstuffs (e.g., fruits, vegetables, nuts, meats, etc.), and water.

In one embodiment, a method of the invention is directed to microbiocidal treatment of textiles. Spores of the Bacillus cereus group have been identified as the predominant post-laundering contaminant of textiles. Thus, the treatment of textiles with a composition of the invention is particularly useful for antimicrobial activity against the contaminants of textiles.

Examples of textiles that can be treated with a composition of the invention include personal items (e.g., shirts, pants, stockings, undergarments, etc.), institutional items (e.g., towels, lab coats, gowns, aprons, etc.), hospitality items (e.g., towels, napkins, tablecloths, etc.), etc.

A microbiocidal treatment of textiles with a composition of the invention can include contacting a textile with a composition of the invention. This contacting can occur prior to laundering the textile. Alternatively, this contacting can occur during laundering of the textile to provide antimicrobial activity and optionally provide cleansing activity to remove or reduce soils, stains, etc. from the textile.

In one embodiment, a textile is contacted with a composition of the invention by mixing a textile with a composition of the invention in a container such as, for example, a wash chamber in a machine washer. Then the textile can be cleaned by washing the textile with a laundering detergent and bleach solutions to remove soil and stains.

In another embodiment, a textile is first rinsed with water at a temperature of about 90° F., and the water is drained. The rinsed textile is then contacted with a composition of the invention at a temperature of about 100° F. and drained.

Any combination of the following steps can also be included after a textile is contacted with a composition of the invention. The textile can be rinsed, for example, rinsed with water at a temperature of about 130° F., and then washed, for example, washed with an alkaline detergent at a temperature of about 160° F. and drained. The textile can be rinsed again, for example, rinsed with water at a temperature of about 160° F. and drained.

The textile can be bleached by, for example, rinsing with hydrogen peroxide at a temperature of about 160° F., drained, and again rinsed with water at a temperature of about 150° F. Preferably any bleaching step carried out occurs after the textile has been contacted with a composition of the invention to avoid allowing microorganisms to build-up resistance to a composition of the invention and/or to avoid exposing a composition of the invention to a pH of greater than 8, which can adversely affect the efficacy of peroxycarboxylic acid.

The textile can be rinsed again at a temperature of about 130° F. and rinsed again at a temperature of about 110° F.

At the end of the cycle, the textile can be rinsed with a pH neutralizing agent, for example, dilute acid.

Because the laundering procedure for textiles varies greatly from industry to industry, a method of treating a textile with a composition is not limited to one particular procedure but can be adapted to be useful in any of the industries identified above. For example, the temperature, number of rinses, bleaching, etc. can vary depending on the substance being laundered.

This invention will be further characterized by the following examples. These examples are not meant to limit the scope of the invention, which has been fully set forth in the foregoing description. Variations within the scope of the invention will be apparent to those skilled in the art.

WORKING EXAMPLES

Example 1

The Effect of Hydrogen Peroxide and Acetic Acid Concentration on the Sporicidal Activity and Kill Rate of Peroxyacetic Acid at 60° C.

Test Method

The rate at which a composition of the invention killed a test organism was measured by inoculating use solutions with a test organism and then quantifying survivors after various exposure times. Ninety-nine mL of each use solution was transferred to a 250 mL Erlenmeyer flask and allowed to equilibrate to test temperature. The liquid in the flask was swirled vigorously in a rapid circular motion, and 1 mL of a suspension of the test organism was added. After the exposure time, 1 mL quantities of the use solution/test organism mixture were transferred to 9 mL of the use-solution neutralizer. The neutralizer was heat shocked for 13 minutes at 80° C. and then cooled rapidly to room temperature.

A use-solution neutralizer terminates the antimicrobial activity of the use solution, thereby allowing the number of survivors to be determined after a set exposure time.

One mL quantities of the neutralizer were pour-plated using the plating medium.

Serial 10-fold or 100-fold dilutions of the neutralizer solution were also plated. Plates were incubated and then surviving microorganisms were counted. The $\text{Log}_{10}$ reduction of the test organism due to the use solution was determined by comparing reduction to an untreated control set (referred to as the Inoculum Numbers).

Method Parameters

A composition containing 34.1 weight-percent peroxyacetic acid (POAA), 7.13 weight-percent hydrogen peroxide ($H_2O_2$), and 36.1 weight-percent acetic acid was first prepared. The composition was then diluted with water to achieve a use solution containing 150 ppm POAA. Additional $H_2O_2$ or acetic acid was added to the use solution to develop use solutions containing $H_2O_2$ and acetic acid in amounts as indicated in Table 1. Table 1 provides the results of duplicate POAA, $H_2O_2$, acetic acid, and pH analyses of each use solution after preparation.

TABLE 1

Analysis of Components of Use Solutions at Equilibrium

Properties After Being Held 40 minutes at 60° C.
(chemical analyses occurred
approximately 2 hours after preparation)

| Use Solution | ppm POAA | ppm $H_2O_2$ | ppm Acetic Acid | pH | POAA:$H_2O_2$ |
|---|---|---|---|---|---|
| A | 147/144 | 31/33 | 174/166 | 3.76/3.67 | 4.7/4.4 |
| B | 145/144 | 33/37 | 346/346 | 3.71/3.55 | 4.4/3.9 |
| C | 151/148 | 277/281 | 141/143 | 3.79/3.69 | 0.6/.5 |
| D | 151/151 | 283/280 | 301/291 | 3.70/3.60 | 0.5/.5 |
| E | 157/154 | 526/514 | 136/148 | 3.81/3.71 | 0.3/.3 |
| F | 160/159 | 533/240* | 293/324 | 3.71/3.62 | 0.3/0.7 |

*No obvious error in analysis was detected, but the result remains in question.

The following experimental parameters were used to determine the effect of hydrogen peroxide and acetic acid concentration on sporicidal activity of peroxyacetic acid. The test organism studied was *Bacillus cereus* #N1009 spore crop (National Food Processors Association). The test temperature was 60° C., and the exposure times were 10, 15, 20, 25, 30, and 40 minutes. The use-solution neutralizer was Fluid Thioglycollate medium (Difco Laboratories, Sparks, Md.) and the cultures were plated on Dextrose Tryptone agar (Difco Laboratories, Sparks, Md.) and incubated for 48 hours at 32° C.

Table 2 shows the results for the untreated microorganisms (control set), and Table 3 shows the results for the treated microorganisms.

Results

TABLE 2

Inoculum Numbers

| Organism | Inoculum Test Replicate (CFU/mL) | | | Average (CFU/mL) |
|---|---|---|---|---|
| | 1 | 2 | 3 | |
| *B. cereus* Spores | $28 \times 10^6$ | $22 \times 10^6$ | $29 \times 10^6$ | $26 \times 10^7$ |

TABLE 3

Reduction of *Bacillus cereus* Spores at 60° C.

| Use Solution | Exposure Time (min.) | Survivors (CFU/mL) | Log Reduction |
|---|---|---|---|
| A | 10 | $<1.0 \times 10^1$ | >6.41 |
| Low Acetic, | 15 | $<1.0 \times 10^1$ | >6.41 |
| Low $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| B | 10 | $<1.0 \times 10^1$ | >6.41 |
| High Acetic, | 15 | $<1.0 \times 10^1$ | >6.41 |
| Low $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| C | 10 | $4.1 \times 10^4$ | 2.80 |
| Low Acetic, | 15 | $2.0 \times 10^2$ | 5.11 |
| Medium $H_2O_2$ | 20 | $<1.0 \times 10^1$ | >6.41 |
| | 25 | $<1.0 \times 10^1$ | >6.41 |
| | 30 | $<1.0 \times 10^1$ | >6.41 |
| | 40 | $<1.0 \times 10^1$ | >6.41 |
| D | 10 | $2.6 \times 10^4$ | 3.00 |
| High Acetic, | 15 | $7.0 \times 10^1$ | 5.57 |
| Medium $H_2O_2$ | 20 | $<1.0 \times 10^1$ | >6.41 |

TABLE 3-continued

Reduction of *Bacillus cereus* Spores at 60° C.

| Use Solution | Exposure Time (min.) | Survivors (CFU/mL) | Log Reduction |
|---|---|---|---|
| | 25 | <1.0 × 10$^1$ | >6.41 |
| | 30 | <1.0 × 10$^1$ | >6.41 |
| | 40 | <1.0 × 10$^1$ | >6.41 |
| E | 10 | 2.4 × 10$^4$ | 3.03 |
| Low Acetic, | 15 | 2.4 × 10$^2$ | 5.03 |
| High H$_2$O$_2$ | 20 | <1.0 × 10$^1$ | >6.41 |
| | 25 | <1.0 × 10$^1$ | >6.41 |
| | 30 | <1.0 × 10$^1$ | >6.41 |
| | 40 | <1.0 × 10$^1$ | >6.41 |
| F | 10 | 1.1 × 10$^4$ | 3.37 |
| High Acetic, | 15 | 7.0 × 10$^1$ | 5.57 |
| High H$_2$O$_2$ | 20 | <1.0 × 10$^1$ | >6.41 |
| | 25 | <1.0 × 10$^1$ | >6.41 |
| | 30 | <1.0 × 10$^1$ | >6.41 |
| | 40 | <1.0 × 10$^1$ | >6.41 |

The results (also represented in FIG. 1) show that the kill rate of peroxyacetic acid, in aqueous solution with acetic acid and hydrogen peroxide, is faster when in the presence of low concentration of hydrogen peroxide relative to the concentration of peroxyacetic acid (as in use solutions A and B). That is, use solutions containing a ratio of peroxyacetic acid to hydrogen peroxide of about 4:1 or greater showed better sporicidal activity in the first 15 minutes of exposure than the other use solutions.

Use solutions C through F contained greater than 100 ppm of hydrogen peroxide and a ratio of peroxyacetic acid to hydrogen peroxide of about 0.7:1 or less. These solutions show a kill rate that is substantially slower than use solutions A and B having a peroxyacetic-acid-to-hydrogen-peroxide ratio of about 4:1 or greater.

The data show, that in the initial period of time after contact, a much more rapid kill of spores is achieved with a modified composition at reduced hydrogen peroxide concentration relative to an unmodified peroxycarboxylic acid. The sharp difference in kill rate of these compositions demonstrates the improved efficacy of a composition of the invention, as compared to a composition containing higher concentrations of hydrogen peroxide relative to peroxycarboxylic acid, against bacterial spores. It is a complete surprise that reducing the hydrogen peroxide relative to peroxycarboxylic acid concentration would increase the rate of spore killing activity.

Example 2

The Effect of Hydrogen Peroxide and Acetic Acid Concentration on the Sporicidal Activity and Kill Rate of Peroxyacetic Acid at 40° C.

Test Method

The test method was carried out as described for Example 1.

Method Parameters

A composition containing 34.1 weight-percent POAA, 7.13 weight-percent H$_2$O$_2$, and 36.1 weight-percent acetic acid was prepared. The composition was then diluted with water to achieve a use solution containing 150 ppm POAA. Additional H$_2$O$_2$ or acetic acid was added to the use solution to develop use solutions containing H$_2$O$_2$ and acetic acid in amounts as indicated in Table 4.

Because the chemical analyses for the use solutions of Example 1 correlated well with the theoretical analyses for the use solutions, this Example relies on the theoretical analyses of the use solutions to determine the concentration of components.

Table 4 shows the theoretical amounts of POAA, H$_2$O$_2$, and acetic acid of each use solution after preparation.

TABLE 4

Analysis of Components of Use Solution at Equilibrium

| Use Solution | ppm POAA | ppm H$_2$O$_2$ | ppm Acetic Acid | pH | POAA: H$_2$O$_2$ |
|---|---|---|---|---|---|
| A | 150 | 31 | 159 | 3.75 | 4.8:1 |
| B | 150 | 31 | 309 | 3.67 | 4.8:1 |
| C | 150 | 275 | 159 | 3.75 | 0.5:1 |
| D | 150 | 275 | 309 | 3.68 | 0.5:1 |
| E | 150 | 529 | 159 | 3.77 | 0.3:1 |
| F | 150 | 529 | 309 | 3.68 | 0.3:1 |

The following experimental parameters were used to determine the effect of hydrogen peroxide and acetic acid concentration on sporicidal efficacy of peroxyacetic acid. The test organism studied was *Bacillus cereus* #N1009 spore crop (National Food Processors Association). The test temperature was 40° C., and the exposure times were 0.5, 1.0, 1.5, 2.0, 2.5, 3.0, and 3.5 hours. The use-solution neutralizer was Fluid Thioglycollate medium, and the cultures were plated on Dextrose Tryptone agar and incubated for 48 hours at 32° C.

Table 5 shows the results for the untreated microorganisms (control set), and Table 6 shows the results for the treated microorganisms.

Results

TABLE 5

| | Inoculum Numbers | | | |
|---|---|---|---|---|
| | Inoculum Test Replicate (CFU/mL) | | | Average |
| Organism | 1 | 2 | 3 | (CFU/mL) |
| *B. cereus* Spores | 30 × 10$^6$ | 26 × 10$^6$ | 26 × 10$^6$ | 2.7 × 10$^7$ |

TABLE 6

Reduction of *Bacillus cereus* Spores at 40° C.

| Use Solution | Exposure Time (hours) | Survivors (CFU/mL) | Log Reduction |
|---|---|---|---|
| A | 0.5 | <1.0 × 10$^1$ | >6.43 |
| Low Acetic, | 1.0 | <1.0 × 10$^1$ | >6.43 |
| Low H$_2$O$_2$ | 1.5 | <1.0 × 10$^1$ | >6.43 |
| | 2.0 | <1.0 × 10$^1$ | >6.43 |
| | 2.5 | <1.0 × 10$^1$ | >6.43 |
| | 3.0 | <1.0 × 10$^1$ | >6.43 |
| | 3.5 | <1.0 × 10$^1$ | >6.43 |
| B | 0.5 | <1.0 × 10$^1$ | >6.43 |
| High Acetic, | 1.0 | <1.0 × 10$^1$ | >6.43 |
| Low H$_2$O$_2$ | 1.5 | <1.0 × 10$^1$ | >6.43 |
| | 2.0 | <1.0 × 10$^1$ | >6.43 |
| | 2.5 | <1.0 × 10$^1$ | >6.43 |
| | 3.0 | <1.0 × 10$^1$ | >6.43 |
| | 3.5 | <1.0 × 10$^1$ | >6.43 |
| C | 0.5 | 1.7 × 10$^7$ | 0.20 |
| Low Acetic, | 1.0 | 6.0 × 10$^6$ | 0.65 |
| Medium H$_2$O$_2$ | 1.5 | 2.5 × 10$^6$ | 1.03 |
| | 2.0 | 9.0 × 10$^5$ | 1.48 |
| | 2.5 | 2.1 × 10$^5$ | 2.11 |
| | 3.0 | 6.0 × 10$^4$ | 2.65 |
| | 3.5 | 1.5 × 10$^4$ | 3.26 |
| D | 0.5 | 1.5 × 10$^7$ | 0.26 |
| High Acetic, | 1.0 | 4.9 × 10$^6$ | 0.74 |
| Medium H$_2$O$_2$ | 1.5 | 2.2 × 10$^6$ | 1.09 |
| | 2.0 | 4.6 × 10$^5$ | 1.77 |
| | 2.5 | 1.2 × 10$^5$ | 2.35 |

TABLE 6-continued

Reduction of Bacillus cereus Spores at 40° C.

| Use Solution | Exposure Time (hours) | Survivors (CFU/mL) | Log Reduction |
|---|---|---|---|
| | 3.0 | $3.1 \times 10^4$ | 2.94 |
| | 3.5 | $1.1 \times 10^4$ | 3.39 |
| E | 0.5 | $1.5 \times 10^7$ | 0.26 |
| Low Acetic, | 1.0 | $5.1 \times 10^6$ | 0.72 |
| High $H_2O_2$ | 1.5 | $1.4 \times 10^6$ | 1.29 |
| | 2.0 | $3.1 \times 10^5$ | 1.94 |
| | 2.5 | $3.4 \times 10^4$ | 2.90 |
| | 3.0 | $4.0 \times 10^3$ | 3.83 |
| | 3.5 | $5.6 \times 10^2$ | 4.68 |
| F | 0.5 | $1.4 \times 10^7$ | 0.29 |
| High Acetic, | 1.0 | $4.7 \times 10^6$ | 0.76 |
| High $H_2O_2$ | 1.5 | $1.7 \times 10^6$ | 1.20 |
| | 2.0 | $4.3 \times 10^5$ | 1.80 |
| | 2.5 | $3.3 \times 10^4$ | 2.91 |
| | 3.0 | $5.0 \times 10^3$ | 3.73 |
| | 3.5 | $8.1 \times 10^2$ | 4.52 |

Figure 2:
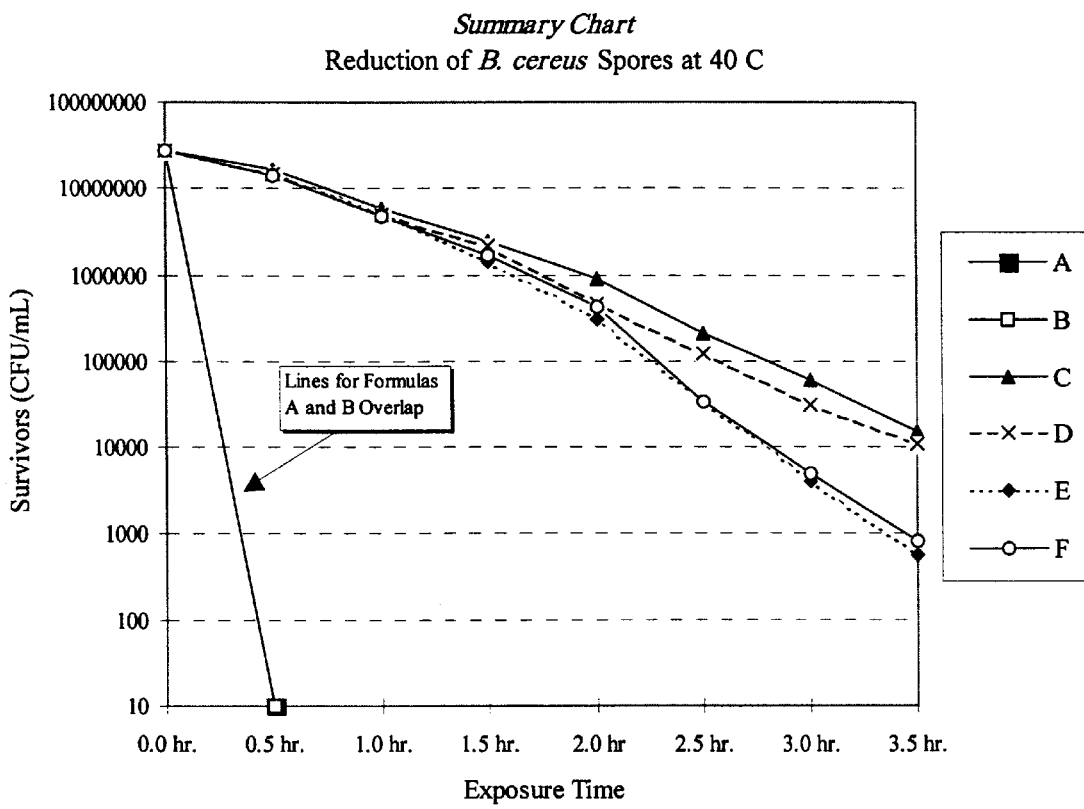
FIG. 2 illustrates the reduction of *Bacillus cereus* spores by modified and unmodified compositions of the invention at 40° C. after variable exposure time to a series of peroxyacetic-acid-containing compositions.

The results (also represented in FIG. 2) show that the kill rate of peroxyacetic acid, in aqueous solution with acetic acid and hydrogen peroxide, is greatest when in the presence of low concentrations of hydrogen peroxide relative to the concentration of peroxyacetic acid (as in use solutions A and B). That is, use solutions containing a ratio of peroxyacetic acid to hydrogen peroxide of greater than about 4:1 showed better sporidical activity over all exposure times than the other use solutions.

Use solutions C through F contained greater than 100 ppm of hydrogen peroxide and a ratio of peroxyacetic acid to hydrogen peroxide of about 0.5:1 or less. These solutions show a kill rate that is substantially slower than use solutions A and B having a ratio of peroxyacetic acid to hydrogen peroxide greater than 4:1.

The data show a much more rapid kill of spores at reduced hydrogen peroxide concentration relative to peroxycarboxylic acid. The sharp difference in kill rate of these compositions demonstrates the improved efficacy of a composition of the invention, as compared to a composition containing higher concentrations of hydrogen peroxide relative to peroxycarboxylic acid, against bacterial spores. It is a complete surprise that reducing the hydrogen peroxide relative to peroxycarboxylic acid concentration would increase the rate of spore killing activity.

Example 3

Verification of the Impact of Hydrogen Peroxide Concentration on the Sporicidal Activity and Kill Rate of Peroxyacetic Acid Test Method The rate at which use solutions of the compositions killed a test organism was measured by inoculating a use solution with a test organism and then quantifying survivors after various exposure times. Ninety-nine mL of each use solution was transferred to a 250 mL Erlenmeyer flask and allowed to equilibrate to test temperature. The liquid in the flask was swirled vigorously in a rapid circular motion and 1 mL of a suspension of the test organism was added.

Three different groups of test organisms were tested against the use solution. Organisms in group 1 were pretreated with 300 ppm $H_2O_2$ for 1 minute. Organisms in group 2 were pretreated with 300 ppm $H_2O_2$ for 10 minutes. And organisms in group 3 were not pretreated.

After the exposure time, 1 mL quantities of the use solution/test organism mixture were transferred to 9 mL of the use-solution neutralizer. The neutralizer was heat shocked for 13 minutes at 80° C. and then cooled rapidly to room temperature. One mL quantities of the neutralizer were pour-plated using the plating medium. Serial 10-fold or 100-fold dilutions of the neutralizer solution were also plated.

Plates were incubated and then surviving microorganisms were counted. The $Log_{10}$ reduction of the test organism due to the use solution was determined by comparing reduction to an untreated control set (referred to as the Inoculum Numbers).

Method Parameters

A composition containing 34.1 weight-percent POAA, 7.13 weight-percent $H_2O_2$, and 36.1 weight-percent acetic acid. The composition was then diluted with water to achieve a use solution containing 150 ppm POAA. Additional $H_2O_2$ or acetic acid was added to the use solution to develop use solutions containing $H_2O_2$ and acetic acid in amounts as indicated in Table 7.

300 ppm hydrogen peroxide solutions were prepared from a stock material (35.29% $H_2O_2$).

TABLE 7

Components of the Use Solution at Equilibrium

| ppm POAA | ppm $H_2O_2$ | ppm Acetic Acid | pH |
|---|---|---|---|
| 150 | 31 | 159 | 3.75 |

The following experimental parameters were used to determine the effect of hydrogen peroxide on sporicidal activity of peroxyacetic acid. The test organism studied was Bacillus cereus #N1009 spore crop (National Food Processors Association). The test temperature was 40° C., and the exposure times were 5, 10, 15, 20, 25, and 30 minutes. The use-solution neutralizer was Fluid Thioglycollate medium, and the cultures were plated on Dextrose Tryptone agar and incubated for 48 hours at 32° C.

Table 8 shows the results for the untreated microorganisms (control set), and Table 9 shows the results for the treated microorganisms.

Results

TABLE 8

Inoculum Numbers

| | Inoculum Test Replicate (CFU/mL) | | | Average |
|---|---|---|---|---|
| Organism | 1 | 2 | 3 | (CFU/mL) |
| B. cereus Spores | $39 \times 10^6$ | $36 \times 10^6$ | $38 \times 10^6$ | $3.8 \times 10^7$ |

TABLE 9

Reduction of Bacillus cereus Spores at 40° C.

| Treatment | Exposure Time (min.) | Survivors (CFU/mL) | Log Reduction |
|---|---|---|---|
| Spores treated with test substance only | 5 | $1.7 \times 10^5$ | 2.35 |
| | 10 | $5.2 \times 10^2$ | 4.86 |
| | 15 | $<1.0 \times 10^1$ | >6.58 |
| | 20 | $<1.0 \times 10^1$ | >6.58 |
| | 25 | $<1.0 \times 10^1$ | >6.58 |
| | 30 | $<1.0 \times 10^1$ | >6.58 |
| Spores treated with 300 ppm $H_2O_2$ for 1 minute, followed by treatment with use solution | 5 | $2.0 \times 10^7$ | 0.28 |
| | 10 | $1.6 \times 10^7$ | 0.38 |
| | 15 | $1.5 \times 10^7$ | 0.40 |
| | 20 | $1.5 \times 10^7$ | 0.40 |
| | 25 | $1.1 \times 10^7$ | 0.54 |

TABLE 9-continued

Reduction of *Bacillus cereus* Spores at 40° C.

| Treatment | Exposure Time (min.) | Survivors (CFU/mL) | Log Reduction |
|---|---|---|---|
|  | 30 | $9.4 \times 10^6$ | 0.61 |
| Spores Treated with 300 ppm | 5 | $1.7 \times 10^7$ | 0.35 |
| $H_2O_2$ for 10 minutes, | 10 | $1.4 \times 10^7$ | 0.43 |
| followed by treatment with | 15 | $1.2 \times 10^7$ | 0.50 |
| use solution | 20 | $1.3 \times 10^7$ | 0.47 |
|  | 25 | $1.1 \times 10^7$ | 0.54 |
|  | 30 | $8.4 \times 10^6$ | 0.66 |

The results show that *Bacillus cereus* spores pretreated with hydrogen peroxide are more resistant to the sporicidal activity of a use solution, indicating that hydrogen peroxide inhibits the sporicidal activity of peroxyacetic acid.

Example 4

The Effect of Hydrogen Peroxide, Octanoic Acid, and Peroxyoctanoic Acid Concentration on the Sporicidal Activity of Peroxyacetic Acid at 40° C.

Test Method

The test method was carried out as described in Example 1.

Method Parameters

A composition containing 33.5 weight-percent POAA, 7.03 weight-percent $H_2O_2$, and 37.2 weight-percentage acetic acid was prepared. A stock solution of octanoic/peroxyoctanoic (11.4% octanoic acid (OA), 2.4% peroxyoctanoic acid (POOA), 10.29% peroxyacetic acid, 3.7% hydrogen peroxide) was also prepared. Additional $H_2O_2$, octanioc acid, or peroxyoctanic acid was added to the use solution to develop use solutions containing $H_2O_2$, octanoic acid, and peroxyoctanoic acid in amounts as indicated in Table 10.

Because the chemical analyses for the use solutions of Example 1 correlated well with the theoretical analyses for the use solutions, this Example on the theoretical analyses of the use solutions.

table 10 shows the theoretical POAA, $H_2O_2$, POOA, octanoic acid, and acetic acid of each use solution after preparation to determine the concentration of components.

TABLE 10

Analysis of Components of Each Use Solution at Equilibrium

| Use Solution | Theoretical ppm POAA | Theoretical ppm $H_2O_2$ | Theoretical ppm AA | Theoretical ppm POOA | Theoretical ppm OA | pH | (POAA + POOA): $H_2O_2$ |
|---|---|---|---|---|---|---|---|
| 1 | 149 | 36 | 282 | 12 | 39 | 3.65 | 4.5:1 |
| 2 | 149 | 529 | 282 | 12 | 39 | 3.62 | 0.3:1 |
| 3 | 149 | 36 | 282 | 50 | 39 | 3.64 | 5.5:1 |
| 4 | 149 | 529 | 282 | 50 | 39 | 3.63 | 0.4:1 |
| 5 | 149 | 36 | 282 | 12 | 138 | 3.64 | 4.5:1 |
| 6 | 149 | 529 | 282 | 12 | 138 | 3.63 | 0.3:1 |
| 7 | 149 | 36 | 282 | 50 | 138 | 3.64 | 5.5:1 |
| 8 | 149 | 529 | 282 | 50 | 138 | 3.65 | 0.4:1 |

The following experimental parameters were used to determine the effect of hydrogen peroxide on sporicidal activity of peroxyacetic acid. The test organism studied was *Bacillus cereus* #N1009 spore crop (National Food Processors Association). The test temperature was 40° C., and the exposure times were 5, 10, 15, 20, 25, and 30 minutes. The use-solution neutralizer was Fluid Thioglycollate medium, and the cultures were plated on Dextrose Tryptone agar and incubated for 48 hours at 32° C.

Table 11 shows the results for the untreated microorganisms (control set), and Table 12 shows the results for the treated microorganisms.

Results

TABLE 11

Inoculum Numbers

| Organism | Inoculum Test Replicate (CFU/mL) | | | Average (CFU/mL) |
|---|---|---|---|---|
|  | 1 | 2 | 3 |  |
| *B. cereus* Spores | $56 \times 10^6$ | $42 \times 10^6$ | $35 \times 10^6$ | $4.4 \times 10^7$ |

TABLE 12

Reduction of *Bacillus cereus* Spores at 40° C.

| Use Solution | Exposure Time (minutes) | Survivors (CFU/mL) | Log Reduction |
|---|---|---|---|
| 1 | 5 | $3.0 \times 10^1$ | 6.17 |
| Low $H_2O_2$, | 10 | $<1.0 \times 10^1$ | >6.64 |
| Low POOA, | 15 | $<1.0 \times 10^1$ | >6.64 |
| Low OA | 20 | $<1.0 \times 10^1$ | >6.64 |
|  | 25 | $<1.0 \times 10^1$ | >6.64 |
|  | 30 | $<1.0 \times 10^1$ | >6.64 |
| 2 | 5 | $6.4 \times 10^6$ | 0.84 |
| High $H_2O_2$, | 10 | $4.3 \times 10^6$ | 1.01 |
| Low POOA, | 15 | $1.8 \times 10^6$ | 1.39 |
| Low OA | 20 | $4.0 \times 10^5$ | 2.04 |
|  | 25 | $1.2 \times 10^5$ | 2.56 |
|  | 30 | $8.1 \times 10^4$ | 2.73 |
| 3 | 5 | $<1.0 \times 10^1$ | >6.64 |
| Low $H_2O_2$, | 10 | $<1.0 \times 10^1$ | >6.64 |
| High POOA, | 15 | $<1.0 \times 10^1$ | >6.64 |
| Low OA | 20 | $<1.0 \times 10^1$ | >6.64 |
|  | 25 | $<1.0 \times 10^1$ | >6.64 |
|  | 30 | $<1.0 \times 10^1$ | >6.64 |
| 4 | 5 | $3.4 \times 10^5$ | 2.11 |
| High $H_2O_2$, | 10 | $1.6 \times 10^4$ | 3.44 |
| Low POOA, | 15 | $1.9 \times 10^3$ | 4.36 |
| Low OA | 20 | $3.0 \times 10^1$ | 6.17 |
|  | 25 | $<1.0 \times 10^1$ | >6.64 |
|  | 30 | $<1.0 \times 10^1$ | >6.64 |
| 5 | 5 | $<1.0 \times 10^1$ | >6.64 |

TABLE 12-continued

Reduction of *Bacillus cereus* Spores at 40° C.

| Use Solution | Exposure Time (minutes) | Survivors (CFU/mL) | Log Reduction |
|---|---|---|---|
| Low $H_2O_2$, | 10 | <$1.0 \times 10^1$ | >6.64 |
| Low POOA, | 15 | <$1.0 \times 10^1$ | >6.64 |
| High OA | 20 | <$1.0 \times 10^1$ | >6.64 |
|  | 25 | <$1.0 \times 10^1$ | >6.64 |
|  | 30 | <$1.0 \times 10^1$ | >6.64 |
| 6 | 5 | $4.4 \times 10^6$ | 1.00 |
| High $H_2O_2$, | 10 | $4.1 \times 10^5$ | 2.03 |
| Low POOA, | 15 | $7.7 \times 10^4$ | 2.76 |
| High OA | 20 | $5.3 \times 10^4$ | 2.92 |
|  | 25 | $1.4 \times 10^4$ | 3.50 |
|  | 30 | $5.8 \times 10^3$ | 3.88 |
| 7 | 5 | <$1.0 \times 10^1$ | >6.64 |
| Low $H_2O_2$, | 10 | <$1.0 \times 10^1$ | >6.64 |
| High POOA, | 15 | <$1.0 \times 10^1$ | >6.64 |
| High OA | 20 | <$1.0 \times 10^1$ | >6.64 |
|  | 25 | <$1.0 \times 10^1$ | >6.64 |
|  | 30 | <$1.0 \times 10^1$ | >6.64 |
| 8 | 5 | $1.2 \times 10^5$ | 2.56 |
| High $H_2O_2$, | 10 | $2.0 \times 10^3$ | 4.34 |
| High POOA, | 15 | $4.0 \times 10^1$ | 6.04 |
| High OA | 20 | <$1.0 \times 10^1$ | >6.64 |
|  | 25 | <$1.0 \times 10^1$ | >6.64 |
|  | 30 | <$1.0 \times 10^1$ | >6.64 |

The results show that the kill rate of peroxyacetic acid, in aqueous solution with acetic acid, octanoic acid, peroxyoctanoic acid, and hydrogen peroxide, is fastest in use solutions containing a ratio of (peroxyacetic acid+peroxyoctanoic acid) to hydrogen peroxide of greater than 4:1 (as in use solutions 1, 3, 5, and 7).

Example 5

Antifungal and AntiBacillus Activity of Peroxyacetic Acid and a Quaternary Ammonium Composition Test Method The rate at which a composition of the invention killed a test organism was measured by inoculating use solutions with a test organism and then quantifying survivors after various exposure times. Ninety-nine mL of each use solution was transferred to a 250 mL Erlenmeyer flask and allowed to equilibrate to test temperature. The liquid in the flask was swirled vigorously in a rapid circular motion and 1 mL of a suspension of the test organism was added.

After the exposure time, 1 mL quantities of the use solution/test organism mixture were transferred to 9 mL of the use-solution neutralizer. One mL quantities of the neutralizer were pour-plated using the plating medium. Serial 10-fold or 100-fold dilutions of the neutralizer solution were also plated. Plates were incubated and then surviving microorganisms were counted. The $Log_{10}$ reduction of the test organism due to the use solution was determined by comparing reduction to an untreated control set (referred to as the Inoculum Numbers).

Method Parameters

A composition containing 5.8 weight-percent POAA, 27.5 weight-percent $H_2O_2$, and/or Alkyl ($C_{12}$–$C_{16}$) Dimethyl Benzyl Ammonium Chloride (50% ADBAC) was prepared. Use solutions were then prepared by diluting the composition with water to achieve a concentration of peroxyacetic acid of 128 ppm.

Table 13 shows the components included in the use solution.

TABLE 13

Analysis of Components of Use Solutions at Equilibrium

| Use Solution | ppm POAA | ppm $H_2O_2$ | ppm ADBAC |
|---|---|---|---|
| 1 | 128 | 533 | 0 |
| 2 | 0 | 0 | 20 |
| 3 | 128 | 533 | 20 |

To determine the antifungal effect of a composition containing peroxyacetic acid and/or a quaternary ammonium compound, the following experimental parameters were used. The test organisms studied were *Candida albicans* ATCC 18804, *Saccharomyces cerevisiae* ATCC 834, *Geotrichum candidum* ATCC 34614, *Zygosaccharomyces bailii* ATCC 60483, *Candida* sp. (field isolate), and an unidentified yeast (field isolate). The test temperature used was 25° C., and the exposure time was 30 seconds. The use-solution neutralizers used were 1% sodium thiosulfate/1% peptone/0.025% catalase (for POAA/$H_2O_2$) (Sigma, St. Louis, Mo.), Chambers neutralizer (for the quaternary ammonium compound) (Difco Laboratories, Sparks, Md.), and 1:1 mixture of the above (for POAA/$H_2O_2$/quaternary ammonium compound).

Microorganisms were plated on Sabourad dextrose agar and incubated for 4 days at 26° C. Table 14 shows the results for the untreated microorganisms (control set), and Tables 15, 16, and 17 show the results for the treated microorganisms.

Results

TABLE 14

Inoculum Numbers

| | Inoculum Test Replicate (CFU/mL) | | Average |
|---|---|---|---|
| Organism | 1 | 2 | (CFU/mL) |
| *C. albicans* | $212 \times 10^4$ | $206 \times 10^4$ | $2.1 \times 10^6$ |
| *S. cerevisiae* | $97 \times 10^4$ | $104 \times 10^4$ | $1.0 \times 10^6$ |
| *G. candidum* | $14 \times 10^5$ | $14 \times 10^5$ | $1.4 \times 10^6$ |
| *Z. bailii* | $160 \times 10^4$ | $182 \times 10^4$ | $1.7 \times 10^6$ |
| *Candida* sp. | $85 \times 10^5$ | $76 \times 10^5$ | $8.1 \times 10^6$ |
| Unidentified yeast | $144 \times 10^4$ | $178 \times 10^4$ | $1.6 \times 10^6$ |

TABLE 15

Effects of Use Solution 1

| Test System | Survivors (cfu/ml) | Average Survivors (cfu/ml) | Log Reduction |
|---|---|---|---|
| *C. albicans* | $17 \times 10^5$ | $1.4 \times 10^6$ | 0.18 |
|  | $11 \times 10^5$ |  |  |
| *S. cerevisiae* | $6 \times 10^5$ | $1.1 \times 10^6$ | 0.00 |
|  | $16 \times 10^5$ |  |  |
| *G. candidum* | $11 \times 10^5$ | $1.4 \times 10^6$ | 0.00 |
|  | $16 \times 10^5$ |  |  |
| *Z. bailii* | $15 \times 10^5$ | $1.8 \times 10^6$ | 0.00 |
|  | $21 \times 10^5$ |  |  |
| *Candida* sp. | $56 \times 10^5$ | $5.2 \times 10^6$ | 0.19 |
|  | $48 \times 10^5$ |  |  |
| Unidentified Yeast | $8 \times 10^5$ | $7.5 \times 10^5$ | 0.33 |
|  | $7 \times 10^5$ |  |  |

TABLE 16

Effects of Use Solution 2

| Test System | Survivors (cfu/ml) | Average Survivors (cfu/ml) | Log Reduction |
|---|---|---|---|
| C. albicans | $166 \times 10^3$ | $1.2 \times 10^5$ | 1.24 |
|  | $76 \times 10^3$ |  |  |
| S. cerevisiae | $9 \times 10^5$ | $9.0 \times 10^5$ | 0.05 |
|  | $9 \times 10^5$ |  |  |
| G. candidum | $14 \times 10^5$ | $1.9 \times 10^6$ | 0.00 |
|  | $23 \times 10^5$ |  |  |
| Z. bailii | $13 \times 10^5$ | $1.4 \times 10^6$ | 0.08 |
|  | $15 \times 10^5$ |  |  |
| Candida sp. | $13 \times 10^5$ | $1.2 \times 10^6$ | 0.83 |
|  | $11 \times 10^5$ |  |  |
| Unidentified Yeast | $7 \times 10^5$ | $7.0 \times 10^5$ | 0.36 |
|  | $7 \times 10^5$ |  |  |

TABLE 17

Effects of Use Solution 3

| Test System | Survivors (cfu/ml) | Average Survivors (cfu/ml) | Log Reduction |
|---|---|---|---|
| C. albicans | $<1 \times 10^1$ | $<1.0 \times 10^1$ | >5.00 |
|  | $<1 \times 10^1$ |  |  |
| S. cerevisiae | $<1 \times 10^1$ | $<1.0 \times 10^1$ | >5.00 |
|  | $<1 \times 10^1$ |  |  |
| G. candidum | $<1 \times 10^1$ | $<1.0 \times 10^1$ | >5.00 |
|  | $<1 \times 10^1$ |  |  |
| Z. bailii | $3 \times 10^1$ | $2.0 \times 10^1$ | 4.93 |
|  | $1 \times 10^1$ |  |  |
| Candida sp. | $<1 \times 10^1$ | $<1.0 \times 10^1$ | >5.00 |
|  | $<1 \times 10^1$ |  |  |
| Unidentified Yeast | $<1 \times 10^1$ | $<1.0 \times 10^1$ | >5.00 |
|  | $<1 \times 10^1$ |  |  |

The results show that the fungicidal activity of peroxyacetic acid, in aqueous solution with acetic acid and hydrogen peroxide, is increased significantly in the presence of relatively low concentrations of quaternary ammonium compound (as in formula 3). Combining peroxyacetic acid and a quaternary ammonium compound results in synergistic fungicidal activity.

Example 6

The Antifungal Activity of Hydrogen Peroxide and Peroxyacetic Acid Independently and in Combination with Didecyl Dimethyl Ammonium Chloride at pH 3, 5, 7, 9 and 11

Test Method

The test method was carried out as described in Example 5.

Method Parameters

A composition containing 5.8 weight-percent POAA and 27.5 weight-percent $H_2O_2$ was prepared. A composition containing 35 weight-percent POAA, 7 weight-percent $H_2O_2$, and Didecyl Dimethyl Ammonium Chloride (80% DDAC) was also prepared. Use solutions were then prepared by diluting the appropriate composition with water to obtain the use solutions shown in Table 18. The pH of all use solutions was adjusted with $H_3PO_4$ or NaOH to achieve the pH shown in Table 18.

TABLE 18

Chemical Properties of Each Use Solution at Equilibrium

| ppm POAA | ppm $H_2O_2$ | ppm DDAC | pH |
|---|---|---|---|
| 0 | 0 | 20 | 3.05 |
| 0 | 0 | 20 | 4.88 |
| 0 | 0 | 20 | 7.10 |
| 0 | 0 | 20 | 8.90 |
| 0 | 0 | 20 | 11.02 |
| 0 | 532 | 0 | 3.15 |
| 0 | 532 | 0 | 5.29 |
| 0 | 532 | 0 | 7.20 |
| 0 | 532 | 0 | 8.96 |
| 0 | 532 | 0 | 10.99 |
| 128 | 20 | 0 | 3.07 |
| 128 | 20 | 0 | 4.91 |
| 128 | 20 | 0 | 7.10 |
| 128 | 20 | 0 | 9.20 |
| 128 | 20 | 0 | 11.10 |
| 128 | 533 | 0 | 3.05 |
| 128 | 533 | 0 | 4.88 |
| 128 | 533 | 0 | 7.10 |
| 128 | 533 | 0 | 8.90 |
| 128 | 533 | 0 | 11.02 |
| 0 | 532 | 20 | 3.08 |
| 0 | 532 | 20 | 5.41 |
| 0 | 532 | 20 | 6.86 |
| 0 | 532 | 20 | 9.06 |
| 0 | 532 | 20 | 10.99 |
| 128 | 20 | 20 | 3.02 |
| 128 | 20 | 20 | 5.13 |
| 128 | 20 | 20 | 7.22 |
| 128 | 20 | 20 | 9.15 |
| 128 | 20 | 20 | 11.07 |
| 128 | 533 | 20 | 3.02 |
| 128 | 533 | 20 | 4.89 |
| 128 | 533 | 20 | 7.14 |
| 128 | 533 | 20 | 9.07 |
| 128 | 533 | 20 | 10.98 |

To determine the antifungal activity of hydrogen peroxide and peroxyacetic independently and in combination with a quaternary ammonium compound, the following experimental perimeters were used. The test organism studied was *Zygosaccharomyces bailii* ATCC 60483.

The test temperature used was 25° C., and the exposure time was 30 seconds. The use-solution neutralizer used was 1% sodium thiosulfate/1% peptone/0.025% catalase (for POAA, $H_2O_2$), Chambers neutralizer (for quaternary ammonium compound), and 1:1 mixture of the above (for POAA/$H_2O_2$/quaternary ammonium compound).

The microorganisms were plated on Sabourad dextrose agar and incubated for 4 days at 26° C.

Table 19 shows the results for the untreated microorganisms (control set), and Tables 20–26 show the results for the treated microorganisms.

Results

TABLE 19

Inoculum Numbers

| | Inoculum Test Replicate (CFU/mL) | | | |
|---|---|---|---|---|
| Organism | 1 | 2 | 3 | Average (CFU/mL) |
| Z. bailii | $80 \times 10^5$ | $70 \times 10^5$ | $72 \times 10^5$ | $7.4 \times 10^6$ |

TABLE 20

Effect of 20 ppm Didecyl Dimethyl Ammonium Chloride

| pH of Use Solution | Survivors (cfu/ml) | Log Reduction |
|---|---|---|
| pH 3 | $9.4 \times 10^6$ | 0.00 |
| pH 5 | $7.1 \times 10^6$ | 0.02 |
| pH 7 | $6.6 \times 10^6$ | 0.05 |
| pH 9 | $4.9 \times 10^6$ | 0.18 |
| pH 11 | $1.5 \times 10^5$ | 1.69 |

TABLE 21

Effect of 128 ppm Peroxyacetic Acid with 20 ppm $H_2O_2$

| pH of Use-Solution | Survivors (cfu/ml) | Log Reduction |
|---|---|---|
| pH 3 | $7.5 \times 10^6$ | 0.00 |
| pH 5 | $7.8 \times 10^6$ | 0.00 |
| pH 7 | $7.5 \times 10^6$ | 0.00 |
| pH 9 | $8.3 \times 10^6$ | 0.00 |
| pH 11 | $7.3 \times 10^6$ | 0.01 |

TABLE 22

Effect of 532 ppm Hydrogen Peroxide

| pH of Use-Solution | Survivors (cfu/ml) | Log Reduction |
|---|---|---|
| pH 3 | $7.5 \times 10^6$ | 0.00 |
| pH 5 | $9.9 \times 10^6$ | 0.00 |
| pH 7 | $7.9 \times 10^6$ | 0.00 |
| pH 9 | $6.8 \times 10^6$ | 0.04 |
| pH 11 | $6.5 \times 10^6$ | 0.06 |

TABLE 23

Effect of 128 ppm Peroxyacetic Acid with 533 ppm $H_2O_2$

| pH of Use Solution | Survivors (cfu/ml) | Log Reduction |
|---|---|---|
| pH 3 | $6.2 \times 10^6$ | 0.08 |
| pH 5 | $8.0 \times 10^6$ | 0.00 |
| pH 7 | $7.1 \times 10^6$ | 0.02 |
| pH 9 | $7.7 \times 10^6$ | 0.00 |
| pH 11 | $6.7 \times 10^6$ | 0.04 |

TABLE 24

Effect of 20 ppm DDAC with 128 ppm Peroxyacetic Acid & 20 ppm $H_2O_2$

| pH of Use Solution | Survivors (cfu/ml) | Average Survivors (cfu/ml) | Log Reduction |
|---|---|---|---|
| pH 3 | $46 \times 10^1$ $107 \times 10^1$ | $7.7 \times 10^2$ | 3.98 |
| pH 5 | $46 \times 10^1$ $50 \times 10^1$ | $4.8 \times 10^2$ | 4.19 |
| pH 7 | $4 \times 10^1$ $29 \times 10^1$ | $1.7 \times 10^2$ | 4.64 |
| pH 9 | $13 \times 10^5$ $14 \times 10^5$ | $1.4 \times 10^6$ | 0.72 |
| pH 11 | $4 \times 10^1$ $13 \times 10^1$ | $8.5 \times 10^1$ | 4.94 |

TABLE 25

Effect of 20 ppm DDAC with 532 ppm Hydrogen Peroxide

| pH of Use Solution | Survivors (cfu/ml) | Average Survivors (cfu/ml) | Log Reduction |
|---|---|---|---|
| pH 3 | $71 \times 10^5$ $70 \times 10^5$ | $7.1 \times 10^6$ | 0.02 |
| pH 5 | $77 \times 10^5$ $93 \times 10^5$ | $8.5 \times 10^6$ | 0.00 |
| pH 7 | $85 \times 10^5$ $72 \times 10^5$ | $7.9 \times 10^6$ | 0.00 |
| pH 9 | $44 \times 10^5$ $35 \times 10^5$ | $4.0 \times 10^6$ | 0.27 |
| pH 11 | $140 \times 10^1$ $174 \times 10^1$ | $1.6 \times 10^3$ | 3.67 |

TABLE 26

20 ppm DDAC with 128 ppm Peroxyacetic Acid and 533 ppm $H_2O_2$

| pH of Use Solution | Survivors (cfu/ml) | Average Survivors (cfu/ml) | Log Reduction |
|---|---|---|---|
| pH 3 | $105 \times 10^1$ $104 \times 10^1$ | $1.0 \times 10^3$ | 3.87 |
| pH 5 | $40 \times 10^1$ $112 \times 10^1$ | $7.6 \times 10^2$ | 3.99 |
| pH 7 | $3 \times 10^1$ $12 \times 10^1$ | $7.5 \times 10^1$ | 4.99 |
| pH 9 | $19 \times 10^5$ $10 \times 10^5$ | $1.5 \times 10^6$ | 0.69 |
| pH 11 | $11 \times 10^1$ $19 \times 10^1$ | $1.5 \times 10^2$ | 4.69 |

The results show that the increased fungicidal activity of peroxyacetic acid, in aqueous solution with acetic acid and hydrogen peroxide combined with a quaternary ammonium compound, is the result of a synergistic activity between peroxyacetic acid and a quaternary ammonium compound. The concentration of hydrogen peroxide present with peroxyacetic acid does not effect synergy with quaternary ammonium compound.

Example 7
The Effect of Hydrogen Peroxide Reduction (by Catalase) and Quaternary Ammonium Compound Addition on the Sporicidal Efficacy of a Peroxyacetic Acid 1 Hydrogen Peroxide Composition Test Method:
The test method was carried out as described in Example 5.

Method Parameters:
A composition containing 15 weight-percent POAA, 11 weight percent $H_2O_2$, Didecyl Dimethyl Ammonium Chloride (80% DDAC), and catalase (catalase from bovine liver—one unit will decompose 1 µmol of $H_2O_2$ per minute at pH 7.0 at 25° C.) (Sigma, St. Louis, Mo.) was prepared. The use solutions tested are shown in Table 27

TABLE 27

Components of Use Solutions in Equilibrium

| Use Solution | Catalase (%) | POAA (ppm) | $H_2O_2$ (ppm) | DDAC (ppm) | POAA: $H_2O_2$ |
|---|---|---|---|---|---|
| A | 0 | 150 | 114 | 0 | 1.3:1 |
| B | 0.025 | 123 | 7 | 0 | 17.6:1 |
| C | 0 | 150 | 114 | 20 | 1.3:1 |
| D | 0.025 | 123 | 7 | 20 | 17.6:1 |

To determine the effect of hydrogen-peroxide reduction by catalase, the following experimental parameters were used. The test organism studied was *Bacillus cereus* spore crop #N1009 (National Food Processors Association). The test temperature used was 40° C., and the exposure times used were 15, 30, 60, and 120 minutes. The use-solution neutralizers used were 33% Chambers & 66% of 1% sodium thiosulfate (Sigma, St. Louis, Mo.).

Microorganisms were plated on Dextrose Tryptone agar and incubated at 35° C. for 48 hours.

Table 28 shows the results for the untreated microorganisms (control set), and Table 29 shows the results for the treated microorganisms.

Results:

TABLE 28

Inoculum Numbers (CFU/mL)

| Test System | A | B | C | Average |
|---|---|---|---|---|
| *B. cereus* | $35 \times 10^6$ | $38\times 10^6$ | $34 \times 10^6$ | $3.6 \times 10^7$ |

TABLE 29

Reduction of *Bacillus cereus* Spores

| Use Solution | Exposure Times (minutes) | Survivors (CFU/mL) | Average Survivors (CFU/mL) | Log Reduction |
|---|---|---|---|---|
| A | 15 | $154, 160 \times 10^5$ | $1.6 \times 10^7$ | 0.35 |
| | 30 | $119, 122 \times 10^5$ | $1.2 \times 10^7$ | 0.48 |
| | 60 | $53, 50 \times 10^5$ | $5.2 \times 10^6$ | 0.84 |
| | 120 | $8, 2 \times 10^5$ | $5.0 \times 10^5$ | 1.86 |
| B | 15 | $124, 154 \times 10^1$ | $1.4 \times 10^3$ | 4.41 |
| | 30 | $19, 5 \times 10^1$ | $1.2 \times 10^2$ | 5.48 |
| | 60 | <10, <10 | <10 | >6.56 |
| | 120 | <10, <10 | <10 | >6.56 |
| C | 15 | $58, 86 \times 10^5$ | $7.2 \times 10^6$ | 0.70 |
| | 30 | $33, 25 \times 10^5$ | $2.9 \times 10^6$ | 1.09 |
| | 60 | $7, 2 \times 10^5$ | $4.5 \times 10^5$ | 1.90 |
| | 120 | $7, 6 \times 10^3$ | $6.5 \times 10^3$ | 3.74 |
| D | 15 | $182, 113 \times 10^1$ | $1.5 \times 10^3$ | 4.38 |
| | 30 | <10, <10 | <10 | >6.56 |
| | 60 | <10, <10 | <10 | >6.56 |
| | 120 | <10, <10 | <10 | >6.56 |

The results show that sporicidal activity of a use solution was increased by the addition of catalase. Thus, sporicidal activity of a composition of the invention is improved as the amount of active hydrogen peroxide is minimized.

Additionally, the sporicidal activity of the use solution containing peroxyacetic acid and hydrogen peroxide, with or without catalase, was improved using a controlled amount of a quaternary ammonium compound.

Example 8

The Effect of Hydrogen Peroxide Reduction (by Catalase) on the Sporicidal Activity of Peroxyacetic Acid Test Method:

The test method was carried out as described in Example 5.

method Parameters:

A composition containing 15 weight-percent POAA, 11 weight-percent $H_2O_2$, and catalase (catalase from bovine liver—one unit will decompose 1 $\mu$mol of $H_2O_2$ per minute at pH 7.0 at 25° C.) was prepared.

The use solutions evaluated are shown in Table 30.

TABLE 30

Components of Use Solution in Equilibrium

| Use Solution | Catalase (%) | POAA (ppm) | $H_2O_2$ (ppm) | POAA: $H_2O_2$ |
|---|---|---|---|---|
| A | 0 | 150 | 114 | 1.3:1 |
| B | 0.025 | 123 | 7 | 17.6:1 |

To determine the effect of hydrogen peroxide reduction on sporicidal activity, the following experimental parameters were used. The test organisms studied were *Bacillus cereus* (spore crop #N1009), *Bacillus mycoides* (spore crop ATCC 6462), and *Bacillus thuringiensis* (spore crop ATCC 10792). The test temperature used was 40° C., and the exposure times were 15, 30, 60, and 120 minutes.

The use-solution neutralizer used was Fluid Thioglycollate broth.

Microorganisms were plated on Dextrose Tryptone agar and incubated for 32° C. for 48 hours.

Table 31 shows the results for the untreated microorganisms (control set), and Tables 32–34 show the results for the treated microorganisms.

Results:

TABLE 31

Inoculum Numbers (CFU/mL)

| Test System | A | B | C | Average |
|---|---|---|---|---|
| *B. cereus* | $21 \times 10^6$ | $17 \times 10^6$ | $24 \times 10^6$ | $2.1 \times 10^7$ |
| *B. mycoides* | $9 \times 10^6$ | $10 \times 10^6$ | $5 \times 10^6$ | $8.0 \times 10^6$ |
| *B. thuringiensis* | $27 \times 10^6$ | $13 \times 10^6$ | $18 \times 10^6$ | $1.9 \times 10^7$ |

TABLE 32

Effect on *Bacillus cereus*

| Use Soultion | Exposure Times (minutes) | Survivors (CFU/mL) | Average Survivors (CFU/mL) | Log Reduction |
|---|---|---|---|---|
| A | 15 | $186, 140 \times 10^5$ | $1.6 \times 10^7$ | 0.12 |
| | 30 | $114, 96 \times 10^5$ | $1.0 \times 10^7$ | 0.32 |
| | 60 | $48, 82 \times 10^5$ | $6.5 \times 10^6$ | 0.51 |
| | 120 | $45, 13 \times 10^5$ | $2.9 \times 10^6$ | 0.86 |
| B | 15 | $106, 140 \times 10^1$ | $1.2 \times 10^3$ | 4.24 |
| | 30 | $5, 3 \times 10^1$ | $4.0 \times 10^1$ | 5.72 |
| | 60 | <10, <10 | <10 | >6.32 |
| | 120 | <10, <10 | <10 | >6.32 |

TABLE 33

Effect on *Bacillus mycoides*

| Use Soultion | Exposure Times (minutes) | Survivors (CFU/mL) | Average Survivors (CFU/mL) | Log Reduction |
|---|---|---|---|---|
| A | 15 | $6, 3 \times 10^3$ | $4.5 \times 10^3$ | 3.25 |
| | 30 | $17, 14 \times 10^1$ | $1.6 \times 10^2$ | 4.70 |
| | 60 | <10, <10 | <10 | >5.90 |
| | 120 | <10, <10 | <10 | >5.90 |
| | 15 | <10, <10 | <10 | >5.90 |
| B | 30 | <10, <10 | <10 | >5.90 |
| | 60 | <10, <10 | <10 | >5.90 |
| | 120 | <10, <10 | <10 | >5.90 |

TABLE 34

| Effect on *Bacillus thuringiensis* | | | | |
|---|---|---|---|---|
| Use Solution | Exposure Times (minutes) | Survivors (CFU/mL) | Average Survivors (CFU/mL) | Log Reduction |
| A | 15 | 34, 33 × $10^5$ | 3.4 × $10^6$ | 0.75 |
| | 30 | 6, 5 × $10^5$ | 5.5 × $10^5$ | 1.54 |
| | 60 | 45, 81 × $10^3$ | 6.3 × $10^4$ | 2.48 |
| | 120 | 104,128 × $10^1$ | 1.2 × $10^3$ | 4.20 |
| B | 15 | 3, 7 × $10^3$ | 5.0 × $10^3$ | 3.58 |
| | 30 | 77, 73 > $10^1$ | 7.5 × $10^2$ | 4.40 |
| | 60 | 12, 11 × $10^1$ | 1.2 × $10^2$ | 5.20 |
| | 120 | <10, <10 | <10 | >6.28 |

The results show that sporicidal activity of a use solution against *Bacillus cereus* group microorganisms was increased by the reduction of hydrogen peroxide with catalase.

Example 9

Antimicrobial Activity of Peroxyacetic Acid Against *Bacillus cereus* Isolated from Surgical Towels Test Method:

The test method was carried out as described in Example 1.

Method Parameters:

Four compositions were prepared:No. 1 (5.8 wt-% POAA, 27.5 wt-% $H_2O_2$), No. 2 (15 wt-% POAA, 11 wt-% $H_2O_2$), No. 3 (35 wt-% POAA, 7 wt-% $H_2O_2$), No. 4 (12 wt-% POAA, 2 wt-% $H_2O_2$). Three use solutions were prepared from each composition. To prepare the use solutions, each composition was diluted in sterile deionized water to result in use solutions containing 150, 200, or 300 ppm POAA.

The use solutions evaluated are shown in Table 35.

TABLE 35

| Components in Use Solution in Equilibrium | | | | |
|---|---|---|---|---|
| Composition # | Use Solution | POAA (ppm) | $H_2O_{(ppm)}$ | POAA: $H_2O_2$ |
| 1 | A | 150 | 711 | 0.2:1 |
| | B | 200 | 948 | |
| | C | 300 | 1422 | |
| 2 | D | 150 | 110 | 1.4:1 |
| | E | 200 | 147 | |
| | F | 300 | 220 | |
| 3 | G | 150 | 30 | 5:1 |
| | H | 200 | 40 | |
| | I | 300 | 60 | |
| 4 | J | 150 | 25 | 6:1 |
| | K | 200 | 33 | |
| | L | 300 | 50 | |

Sodium hypochlorite compositions were also prepared to compare to the peroxyacetic acid compositions. Sodium hypochlorite is a commonly used sanitizer for laundry applications. The sodium hypochlorite compositions were prepared from a stock material containing 5.5% sodium hypochlorite. The stock solution was diluted in sterile deionized water to result in use solutions containing 63, 120, or 155 ppm total available chlorine.

To evaluate the antimicrobial activity against *Bacillus cereus* isolated from surgical towels, the following experimental parameters were used. The test organism studied was *Bacillus cereus* (isolated from a surgical towel). The test temperature used was 100±5° F., and the exposure time was 5 or 10 minutes.

The use-solution neutralizer used was 0.1% sodium thiosulfate+0.5% Tween 80. The microorganisms were plated on tryptone glucose extract agar and incubated at 32° C. for 48 hours.

Table 36 shows the results for the test method.

Results:

TABLE 36

| Effect on *Bacillus cereus* (Field Isolate) | | |
|---|---|---|
| Use Solution | Exposure Time (minutes) | Log Reduction |
| A | 5 | 0.62 |
| | 10 | 0.75 |
| B | 5 | 0.15 |
| | 10 | 0.25 |
| C | 5 | 0.77 |
| | 10 | 0.87 |
| D | 5 | 0.55 |
| | 10 | 0.55 |
| E | 5 | 0.62 |
| | 10 | 0.59 |
| F | 5 | 0.49 |
| | 10 | 0.59 |
| G | 5 | 0.12 |
| | 10 | 0.83 |
| H | 5 | 0.47 |
| | 10 | 1.03 |
| I | 5 | 1.71 |
| | 10 | 4.37 |
| J | 5 | 0.38 |
| | 10 | 0.69 |
| K | 5 | 0.46 |
| | 10 | 1.17 |
| L | 5 | 1.09 |
| | 10 | 2.86 |
| Chlorine | 5 | 0.14 |
| 63 ppm available Cl | 10 | 0.23 |
| Chlorine | 5 | 0.26 |
| 120 ppm available Cl | 10 | 0.33 |
| Chlorine | 5 | 0.20 |
| 155 ppm available Cl | 10 | 0.26 |

Results show that use solutions with low hydrogen peroxide relative to peroxyacetic acid were able to reduce the numbers of *Bacillus cereus* isolated from a surgical towel faster than formulas with higher concentrations of hydrogen peroxide relative to peroxyacetic acid and faster than sodium hypochlorite.

Example 10

The Activity of Peroxyacetic Acid Against *Bacillus cereus* on Surgical Towels

Test Method:

To determine the antimicrobial activity of compositions against *Bacillus cereus* on surgical towels, the following experimental method was used. Towels were inoculated with approximately $10^7$ CFU/towel of *Bacillus cereus* spores (isolated from a surgical towel) by placing ½ml portions of a spore suspension (10 ml of $10^6$ CFU/ml spore suspension) in 20 random areas on each towel. Each towel was then allowed to air dry for approximately 24 hours.

Three towels were each diluted in neutralizer, massaged thoroughly by hand for 1 minute, and plated to determine the initial inoculum present on the towels prior to beginning the wash cycle. These three towels were used as the control set.

Six inoculated towels were tested for each use solution. Towels were first rinsed with 90° F. water for about 5 minutes, and the water was drained. Towels were then rinsed with 1000 F use solution or hot water control for about 10 minutes, and the use solution was drained.

The use solutions tested are shown in Table 37.

TABLE 37

Components of Use Solution at Equilibrium

| Composition | POAA (ppm) | $H_2O_2$ (ppm) | POAA:$H_2O_2$ |
|---|---|---|---|
| 12% POAA, 2% $H_2O_2$ | 150 | 25 | 6:1 |
| | 200 | 33 | 6:1 |
| | 300 | 50 | 6:1 |

The towels were placed in a washing machine with 30 lbs of noninoculated terry towels, and the wash cycle was begun.

Three of the six towels were sampled after a 10 minute exposure time to water for the control set or to the use solution (for experimental towels) and added to a bag containing 400 mL use-solution neutralizer(0.1% sodium thiosulfate±0.5% Tween 80). The average weight of a wet towel was determined to be approximately 100 g. The total weight was then approximately 500 g.

Towels were massaged for 1 minute by hand, and then 1:100 and 1:10,000 dilutions were plated (final dilutions of the plates were 1:500, 1:50,000, 1:5,000,000) by the pour-plate technique onto Typtone Glucose Extract agar and incubated at 32° C. for 48 hours.

The results are shown in Tables 38 and 39.
Results:

TABLE 38

Reduction of *Bacillus cereus* on Surgical Towels

| Use Solution | Log Reduction Over Untreated Control |
|---|---|
| Water Control | 1.16 |
| 150 ppm POAA | 2.51 |
| 200 ppm POAA | 4.77 |
| 300 ppm POAA | 4.71 |

TABLE 39

Reduction of *Baclllus cereus* in Wash Water

| Use Solution | Aerobic Plate Count (CFU/mL) | Log Reduction Over Water Control |
|---|---|---|
| Water control | $3.9 \times 10^3$ | — |
| 150 ppm POAA | $2.6 \times 10^1$ | 2.18 |
| 200 ppm POAA | <1 | >3.59 |
| 300 ppm POAA | <1 | >3.59 |

These results show that the compositions provided reduction of *Bacillus cereus* on textiles.

It should be noted that, as used in this specification and the appended claims, the singular forms "a," "an," and "the" include plural referents unless the content clearly dictates otherwise. Thus, for example, reference to a composition containing "a carboxylic acid" includes a mixture of two or more carboxylic acids.

Although embodiments of the invention have been described above, it is not limited thereto, and it will be apparent to persons skilled in the art that numerous modifications and variations form part of the present invention insofar as they do not depart from the spirit, nature, and scope of the claimed and described invention.

We claim:

1. A composition having antimicrobial activity, the composition comprising an effective antimicrobial amount of a mixture of:

(a) about 0.2 wt-% to about 6 wt-% hydrogen peroxide;

(b) about 0.5 wt-% to about 80 wt-% carboxylic acid of the formula: $R(COOH)_n$, wherein R comprises hydrogen, alkyl, alkenyl, alicyclic group, aryl, heteroaryl, or heterocyclic group, and n is 1, 2, or 3;

(c) about 0.2 wt-% to about 30 wt-% peroxycarboxylic acid of the formula: $R(COOOH)_n$, wherein R comprises hydrogen, alkyl, alkenyl, alicyclic group, aryl, heteroaryl, or heterocyclic group, and n is 1, 2, or 3; and (d) about 0.15 wt-% to 4 wt-% quaternary ammonium compound comprising N-alkyl dimethyl ethyl benzyl ammonium, di-n-alkyl dimethyl ammonium, di-n-alkyl methyl benzyl ammonium salt, or a mixture thereof;

the composition comprising 5 to 18 parts by weight of the peroxycarboxylic acid for each part of hydrogen peroxide;

wherein the composition, employed at a concentration of about 150 ppm peroxycarboxylic acid, causes greater than 5-log reduction in spores of a microorganism of *Bacillus cereus* group in about 10 min at 40° C.

2. The composition of claim 1, wherein the quaternary ammonium compound comprises didecyl dimethyl ammonium.

3. The composition of claim 1, wherein the peroxycarboxylic acid comprises peroxyacetic acid, peroxyoctanoic acid, peroxypropionic acid, peroxybutyric acid, peroxyglycolic acid, peroxyglutaric acid, peroxysuccinic acid, peroxylactic acid, peroxycitric acid, peroxydecanoic acid, peroxyformic acid, peroxypentanoic acid, peroxyheptanoic acid, peroxynonanoic acid, peroxyundecanoic acid, peroxydodecanoic acid, or mixtures thereof.

4. The composition of claim 1, wherein the peroxycarboxylic acid comprises an R that is $C_{1-4}$ alkyl.

5. The composition of claim 4, further comprising a peroxycarboxylic acid comprising an R that is $C_{5-12}$ alkyl.

6. The composition of claim 5, wherein in the composition the peroxycarboxylic acid comprising R that is $C_{5-2}$ alkyl is present in an amount of between about 3 ppm and about 500 ppm.

7. The composition of claim 5, wherein the composition is a concentrate composition and the peroxycarboxylic acid comprising said R that is $C_{5-12}$ alkyl is present in an amount of between about 0.5 weight percent and about 25 weight percent.

8. The composition of claim 5, wherein the composition comprises peroxyacetic acid and peroxyoctanoic acid.

9. The composition of claim 1, further comprising stabilizing agent, hydrotrope, surfactant, or mixture thereof.

10. The composition of claim 9, wherein the stabilizing agent comprises a phosphonic acid or salt thereof.

11. The composition of claim 10, wherein the stabilizing agent comprises 1-hydroxyethylidene-1,1-diphosphonic acid or salt thereof.

12. The composition of claim 1, wherein there are greater than five parts by weight of peroxycarboxylic acid for each part by weight hydrogen peroxide.

13. The composition of claim 1, further comprising adjuvant.

14. The composition of claim 1, wherein the adjuvant comprises inorganic acid.

15. The composition of claim 1, further comprising peroxide destroying agent.

16. The composition of claim 14, wherein the inorganic acid comprises phosphoric acid, phosphonic acid, sulfuric acid, sulfonic acid, nitric acid, or sulfamic acid.

17. A concentrate composition having antimicrobial activity, the composition comprising:

(a) hydrogen peroxide in an amount of between about 0.2 weight percent and about 6 weight percent;

(b) a carboxylic acid of the formula: $R(COOH)_n$, wherein R comprises hydrogen, alkyl, alkenyl, alicyclic group, aryl, heteroaryl, or heterocyclic group, and n is 1, 2, or 3, the carboxylic acid being present in an amount of between about 0.5 weight percent and about 80 weight percent;

(c) a peroxycarboxylic acid of the formula: $R(COOOH)_n$, wherein R comprises hydrogen, alkyl, alkenyl, alicyclic group, aryl, heteroaryl, or heterocyclic group, and n is 1, 2, or 3, the peroxycarboxylic acid being present in an amount of between about 0.2 weight percent and about 30 weight percent; and (d) about 0.15 wt-% to 4 wt-% quaternary ammonium compound comprising N-alkyl dimethyl ethyl benzyl ammonium, di-n-alkyl dimethyl ammonium, di-n-alkyl methyl benzyl ammonium salt, or a mixture thereof;

wherein the composition, employed at a concentration of about 150 ppm peroxycarboxylic acid, causes greater than 5-log reduction in spores of a microorganism of *Bacillus cereus* group in about 10 min at 40° C.

18. The composition of claim 17, wherein there are greater than six parts by weight of peroxycarboxylic acid for each part by weight hydrogen peroxide.

19. The composition of claim 17, wherein the composition comprises hydrogen peroxide in an amount of between about 0.5 weight percent and about 5 weight percent.

20. The composition of claim 17, wherein the composition comprises the carboxylic acid in an amount of between about 10 weight percent and about 70 weight percent.

21. The composition of claim 17, wherein the composition comprises the peroxycarboxylic acid in an amount of between about 2.5 weight percent and about 25 weight percent.

22. The composition of claims 17, wherein the peroxycarboxylic acid comprises peroxyacetic acid, peroxyoctanoic acid, peroxypropionic acid, peroxybutyric acid, peroxyglycolic acid, peroxyglutaric acid, peroxysuccinic acid, peroxylactic acid, peroxycitric acid, peroxydecanoic acid, peroxyformic acid, peroxypentanoic acid, peroxyheptanoic acid, peroxynotianoic acid, peroxyundecanoic acid, peroxydodecanoic acid, or mixtures thereof.

23. The composition of claim 17, wherein the peroxycarboxylic acid comprises an R that is C1-4 alkyl.

24. The composition of claim 23, further comprising a peroxycarboxylic acid comprising an R that is $C_{5-12}$ alkyl.

25. The composition of claim 24, wherein the peroxycarboxylic acid comprising said R that is $C_{5-12}$ alkyl is present in an amount of between about 0.3 weight percent and about 5 weight percent.

26. The composition of claim 24, wherein the composition comprises peroxyacetic acid and peroxyoctanoic acid.

27. The composition of claim 17, further comprising hydrotrope, surfactant, or mixture thereof;

the composition having activity against a fungi.

28. The composition of claim 17, further comprising phosphonic acid or salt thereof.

29. The composition of claim 17, wherein the composition is diluted with water to provide a use solution, the use solution comprising:

(a) hydrogen peroxide in an amount of up to about 2500 ppm;

(b) the carboxylic acid in an amount of between about 2 ppm and about 27000 ppm; and (c) the peroxycarboxylic acid in an amount of between about 1 ppm and about 10000 ppm.

30. The composition of claim 29, wherein the composition is diluted with water at a ratio of about one ounce to six gallons of water.

31. The composition of claim 17, further comprising adjuvant.

32. The composition of claim 31, wherein the adjuvant comprises inorganic acid.

33. The composition of claim 32, wherein the inorganic acid comprises phosphoric acid, phosphonic acid, sulfuric acid, sulfonic acid, nitric acid, or sulfamic acid.

34. A method of reducing the population of spore forming vegetative bacteria and related bacterial spores, the method comprising:

contacting a surface of a substance contaminated by said vegetative bacteria and bacterial spores with an antimicrobial composition;

the surface comprising a surface in a health care environment, in a food environment, in a hospitality environment, in an education environment, or a combination thereof;

the antimicrobial composition comprising an effective antimicrobial amount of a mixture of:

(a) hydrogen peroxide;

(b) carboxylic acid of the formula: $R(COOH)_n$, wherein R comprises hydrogen, alkyl, alkenyl, alicyclic group, aryl, heteroaryl, or heterocyclic group, and n is 1,2, or 3; and (c) peroxycarboxylic acid of the formula: $R(COOOH)_n$, wherein R comprises hydrogen, alkyl, alkenyl, alicyclic group, aryl, heteroaryl, or heterocyclic group, and n is 1, 2, or 3; and 0.15 wt-% to 4 wt-% quaternary ammonium compound comprising N-alkyl dimethyl ethyl benzyl ammonium, di-n-alkyl dimethyl ammonium, di-n-alkyl methyl benzyl ammonium salt, or a mixture thereof;

the composition comprising 5 to 18 parts by weight of the peroxycarboxylic acid for each part of hydrogen peroxide; and reducing the population of spores on the surface of the substance by one log or more after about 10 or fewer minutes of contact.

35. The method of claim 34, wherein the vegetative bacteria and bacterial spores comprise *Bacillus cereus, Bacillus mycoides, Bacillus anthracis, Bacillus thuringiensis*, or mixtures thereof.

36. The method of claim 34, wherein the surface contacted is in a health-care environment.

37. The method of claim 34, wherein the health-care environment comprises a human hospital, an animal hospital, a human clinic, an animal clinic, a nursing home, or a day-care facility.

38. The method of claim 34, wherein the surface contacted is in a food environment.

39. The method of claim 38, wherein the food environment comprises a restaurant, a food-processing plant, a food-storage plant, or a grocery store.

40. The method of claim 34, wherein the surface contacted is in a hospitality environment.

41. The method of claim 34, wherein the hospitality environment comprises a hotel, a motel, a resort, or a cruise ship.

42. The method of claim 34, wherein the surface contacted is in an education environment, the education environment comprising a-school or a university.

43. The method of claim 34, wherein the surface comprises a ceiling, furniture, or a mixture thereof.

44. The method of claim 34, wherein the surface comprises a specific-equipment surface.

45. The method of claim 44, wherein the specific-equipment surface comprises a hard surface, manufacturing equipment, or a mixture thereof.

46. The method of claim 34, wherein the substance treated comprises wood or cellulose-based systems.

47. The method of claim 34, wherein the substance treated comprises foodstuffs.

48. The method of claim 34, wherein the substance comprises soil, the soil being present on a cooling tower, a flume, a hard surface, a foodstuff, or a mixture thereof.

49. The method of claim 34, wherein the substance comprises water.

50. The method of claim 34, wherein the substance contacted comprises polyester.

51. A method of reducing the population of vegetative bacteria and bacterial spores on a textile, the method comprising:
contacting the textile with an antimicrobial composition;
the textile comprising cotton, wool, silk, synthetic fabric, or mixture thereof;
the antimicrobial composition comprising an effective antimicrobial amount of a mixture of:
(a) hydrogen peroxide;
(b) carboxylic acid of the formula: R(COOH)$_n$, wherein R comprises hydrogen, alkyl, alkenyl, alicyclic group, aryl, heteroaryl, or heterocyclic group, and n is 1, 2, or 3; and
(c) peroxycarboxylic acid of the formula: R(COOOH)$_n$, wherein R comprises hydrogen, alkyl, alkenyl, alicyclic group, aryl, heteroaryl, or heterocyclic group, and n is 1, 2, or 3; and
(d) about 0.15 wt-% to 4 wt-% quaternary ammonium compound comprising N-alkyl dimethyl ethyl benzyl ammonium, di-n-alkyl dimethyl ammonium, di-n-alkyl methyl benzyl ammonium salt, or a mixture thereof;
the composition comprising 5 to 18 parts by weight of the peroxycarboxylic acid for each part of hydrogen peroxide; and
reducing the population of spores on the surface of the substance by one log or more after about 10 or fewer minutes of contact.

52. The method of claim 51, wherein the spore or related spore-forming microorganism comprise *Bacillus cereus, Bacillus mycoides, Bacillus anthracis, Bacillus thuringiensis*, or mixtures thereof.

53. The method of claim 51, wherein the textile comprises personal clothing.

54. The method of claim 51, wherein the textile comprises textiles found in a health-care environment, a hospitality environment, or a food environment.

55. The method of claim 51, wherein the textile is from a health-care environment, the textile comprising a towel, bedding, a lab coat, a hospital gown or apron.

56. The method of claim 54, wherein the textile is from a hospitality environment, the textile comprising bedding or a towel.

57. The method of claim 54, wherein the textile is from the food environment, the textile comprising a napkin or a tablecloth.

58. A composition comprising:
about 0.2 to about 6 wt-% hydrogen peroxide;
about 0.5 to about 70 wt-% acetic acid, propionic acid, heptanoic acid, octanoic acid, nonanoic acid, lactic acid, or mixture thereof;
about 2.5 to about 25 wt-% peroxyacetic acid, peroxypropionic acid, peroxyheptanoic acid, peroxyoctanoic acid, peroxynonanoic acid, peroxylactic acid, or mixture thereof, and about 0.15 to about 4 wt-% of N-alkyl dimethyl benzyl ammonium salt, N-alkyl methyl ethyl benzyl ammonium salt, di-n-alkyl dimethyl ammonium salt, di-n-alkyl methyl benzyl ammonium salt, or mixture thereof, in which each alkyl independently contains from 1 to 20 carbon atoms or is an oxyalkyl having from 1 to 8 carbon atoms;
the composition comprising 5 to 18 parts by weight of the peroxycarboxylic acid for each part of hydrogen peroxide;
wherein the composition, employed at a concentration of about 150 ppm peroxycarboxylic acid, causes greater than 5-log reduction in spores of a microorganism of *Bacillus cereus* group in about 10 min at 40° C.

59. The composition of claim 58, comprising 6 to 18 parts by weight of the peroxycarboxylic acid for each part of the hydrogen peroxide.

60. The composition of claim 59, comprising 7 to 18 parts by weight of the peroxycarboxylic acid for each part of hydrogen peroxide.

61. A composition comprising:
about 3 to about 1850 ppm hydrogen peroxide;
about 100 to about 21,000 ppm acetic acid, propionic acid, heptanoic acid, octanoic acid, nonanoic acid, lactic acid, or mixture thereof;
about 100 to about 21000 ppm peroxyacetic acid, peroxypropionic acid, peroxyheptanoic acid, peroxyoctanoic acid, peroxynonanoic acid, peroxylactic acid, or mixture thereof; and
about 10 to about 50 ppm of N-alkyl dimethyl benzyl ammonium salt, N-alkyl methyl ethyl benzyl ammonium salt, di-n-alkyl dimethyl ammonium salt, di-n-alkyl methyl benzyl ammonium salt, or mixture thereof, in which each alkyl independently contains from 1 to 20 carbon atoms or is an oxyalkyl having from 1 to 8 carbon atoms;
the composition comprising 5 to 18 parts by weight of the peroxycarboxylic acid for each part of hydrogen peroxide;
wherein the composition causes greater than 5-log reduction in spores of a microorganism of *Bacillus cereus* group in about 10 min at 40° C.

62. The composition of claim 61, comprising 6 to 18 parts by weight of the peroxycarboxylic acid for each part of hydrogen peroxide.

63. The composition of claim 62, comprising 7 to 18 parts by weight of the peroxycarboxylic acid for each part of the hydrogen peroxide.

64. A composition having antimicrobial activity, the composition comprising an effective antimicrobial amount of a mixture of:
(a) up to about 2500 ppm hydrogen peroxide;
(b) about 2 ppm to about 27000 ppm carboxylic acid of the formula: R(COOH)$_n$, wherein R comprises hydrogen, alkyl, alkenyl, alicyclic group, aryl, heteroaryl, or heterocyclic group, and n is 1, 2, or 3;
(c) about 1 ppm to about 10000 ppm peroxycarboxylic acid of the formula: R(COOOH)$_n$, wherein R comprises hydrogen, alkyl, alkenyl, alicyclic group, aryl, heteroaryl, or heterocyclic group, and n is 1, 2, or 3; and
(d) about 4 ppm to about 100 ppm quaternary ammonium compound comprising N-alkyl dimethyl ethyl benzyl ammonium, di-n-alkyl dimethyl ammonium, di-n-alkyl methyl benzyl ammonium salt, or a mixture thereof,
the composition comprising 5 to 18 parts by weight of the peroxycarboxylic acid for each part of hydrogen peroxide;

wherein the composition, employed at a concentration of about 150 ppm peroxycarboxylic acid, causes greater than 5-log reduction in spores of a microorganism of *Bacillus cereus* group in about 10 min at 40° C.

65. The composition of claim 64, wherein the composition comprises the carboxylic acid in an amount of between about 50 ppm and about 5